(12) United States Patent
Bhatia et al.

(10) Patent No.: US 10,801,015 B2
(45) Date of Patent: Oct. 13, 2020

(54) SYSTEMS AND METHODS FOR CULTURING EPITHELIAL CELLS

(71) Applicants: The Broad Institute, Inc., Cambridge, MA (US); Massachusetts Institute of Technology, Cambridge, MA (US)

(72) Inventors: Sangeeta Bhatia, Lexington, MA (US); Jing Shan, Cambridge, MA (US); Anne Carpenter Van Dyk, Ashland, MA (US); David Logan, Maynard, MA (US); Nathan Ross, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 323 days.

(21) Appl. No.: 14/772,210

(22) PCT Filed: Mar. 14, 2014

(86) PCT No.: PCT/US2014/028219
§ 371 (c)(1),
(2) Date: Sep. 2, 2015

(87) PCT Pub. No.: WO2014/143998
PCT Pub. Date: Sep. 18, 2014

(65) Prior Publication Data
US 2016/0017283 A1    Jan. 21, 2016

Related U.S. Application Data

(60) Provisional application No. 61/791,798, filed on Mar. 15, 2013.

(51) Int. Cl.
*C12N 5/071* (2010.01)
*C12Q 1/04* (2006.01)

(52) U.S. Cl.
CPC ............ *C12N 5/067* (2013.01); *C12Q 1/04* (2013.01); *C12N 2502/1323* (2013.01); *C12N 2531/00* (2013.01)

(58) Field of Classification Search
None
See application file for complete search history.

(56) References Cited

U.S. PATENT DOCUMENTS

| | | | |
|---|---|---|---|
| 7,470,424 B2 * | 12/2008 | Kataoka | C12N 5/0671 424/93.1 |
| 2002/0182633 A1 | 12/2002 | Chen et al. | |
| 2008/0220516 A1 | 9/2008 | Eddington et al. | |

OTHER PUBLICATIONS

Kane, Bartholomew J., et al. "Liver-specific functional studies in a microfluidic array of primary mammalian hepatocytes." Analytical Chemistry 78.13 (2006): 4291-4298. (Year: 2006).*
Cho, Cheul H., et al. "Oxygen uptake rates and liver-specific functions of hepatocyte and 3T3 fibroblast co-cultures." Biotechnology and bioengineering 97.1 (2007): 188-199. (Year: 2007).*
Cho, Cheul H., et al. "A new technique for primary hepatocyte expansion in vitro." Biotechnology and bioengineering 101.2 (2008): 345-356. (Year: 2008).*
Runnegar, Maria T., et al. "Inhibition of reduced glutathione synthesis by cyanobacterial alkaloid cylindrospermopsin in cultured rat hepatocytes." Biochemical pharmacology 49.2 (1995): 219-225 (Year: 1995).*
Bhandari, Rena NB, et al. "Liver tissue engineering: a role for co-culture systems in modifying hepatocyte function and viability." Tissue engineering 7.3 (2001): 345-357. (Year: 2001).*
Khetani, Salman R., et al. "Exploring interactions between rat hepatocytes and nonparenchymal cells using gene expression profiling. " Hepatology 40.3 (2004): 545-554. (Year: 2004).*
Cho, Cheul H., et al. "Layered patterning of hepatocytes in co-culture systems using microfabricated stencils." Biotechniques 48.1 (2010): 47-52 (Year: 2010).*
Khetani, Salman R., and Sangeeta N. Bhatia. "Microscale culture of human liver cells for drug development." Nature biotechnology 26.1 (2008): 120. (Year: 2008).*
Corning® Cell Culture Selection Guide, Corning Incorporated 2002 (Year: 2002).*
Barbaric et al., "Novel regulators of stem cell fates identified by a multivariate phenotype screen of small compounds on human embryonic stem cell colonies," Stem Cell Research, vol. 5, pp. 104-119, May 2010.
Cho et al., "A New Technique for Primary Hepatocyte Expansion in Vitro," Biotechnology and Bioengineering, vol. 101, No. 2, pp. 345-356, Mar. 24, 2008, entire document.
Wegrowski et al., "Stimulation of sulphated glycosaminoglycan and decorin production in adult dermal fibroblasts by recombinant human interleukin-4," Biochemical Journal, vol. 307, pp. 673-678, 1995, entire document.
Notara et al., "A xenobiotic-free culture system for human limbal epithelial stem cells," Regenerative Medicine, vol. 2, No. 6, pp. 919-927, Nov. 2007, entire document.
Albrecht et al., "Microfluidics-integrated time-lapse imaging for analysis of cellular dynamics," Integrative Biology, vol. 2, pp. 278-287, entire document.
Notification of Transmittal of the International Search Report and the Written Opinion of the International Searching Authority, for corresponding PCT/US2014/028219, dated Jul. 21, 2014 (13 pages).

* cited by examiner

*Primary Examiner* — Robert J Yamasaki
(74) *Attorney, Agent, or Firm* — Melissa Hunter-Ensor; Leslie Serunian; Greenberg Traurig, LLP

(57) ABSTRACT

The present invention features assays for co-culturing primary cells while maintaining key biological activities specific to the primary cells. The invention is based, at least in part, on the discovery that compositions and methods for primary cells in a high-throughput co-culture platform, image analysis for distinguishing cells in co-cultures and assays that are suitable for screening of agents in epithelial cells, such as hepatocytes.

22 Claims, 15 Drawing Sheets

SYSTEMS AND METHODS FOR CULTURING EPITHELIAL CELLS

CROSS-REFERENCE TO RELATED APPLICATION

This application is the U.S. national phase application, pursuant to 35 U.S.C. § 371, of PCT international application Ser. No.: PCT/US2014/028219, filed Mar. 14, 2014, designating the United States and published in English, which claims the benefit of the following U.S. Provisional Application No. 61/791,798, filed Mar. 15, 2013, entitled "Systems and Methods for Culturing Epithelial Cells," the entire contents of which are incorporated herein by reference.

STATEMENT OF RIGHTS TO INVENTIONS MADE UNDER FEDERALLY SPONSORED RESEARCH

This invention was made with government support under Grant Nos. HG005032, DK065152, DK56966, and GM089652 awarded by the National Institutes of Health. The government has certain rights in the invention.

BACKGROUND OF THE INVENTION

Chronic liver disease affects more than 500 million people worldwide. The lack of efficacious treatment options for liver disease is a critical unmet medical need. Most treatments for liver disease are palliative. The only therapy shown to directly alter outcome and prevent mortality is organ transplantation, but its utility is limited by a persistent shortage of donor organs and potential complications arising from host-graft rejection. The deficit of treatment options is further compounded by the absence of a predictive in vitro hepatocyte model, a critical tool for advancing the discovery and development of new drugs to treat liver disease.

The universal utility of a predictive in vitro hepatocyte model is shared across drug development efforts and not limited to drug development for liver disease. A third of drug withdrawals from the market and more than half of all warning labels on drugs approved for a variety of indications are primarily due to adverse affects on the liver. Moreover, the majority of new drug candidates fail in Phase I clinical trials due to issues with liver toxicity and bioavailability of drug candidates indicating that current in vitro liver models used by the pharmaceutical industry, though useful in a limited capacity, are not fully predictive of in vivo liver metabolism and toxicity.

Historically cell culture techniques have failed to take into account the necessary microenvironment for cell-cell and cell-matrix communication. Hepatocytes in particular are notoriously difficult to maintain in culture as they rapidly lose viability and phenotypic functions. Moreover, the typically complex and multi-layered culture systems that work effectively are hard to replicate in miniature, as is needed for preparing such cultures in multi-well plate formats for high-throughput screening. While some progress has been made in culturing isolated primary human hepatocytes, adapting these in vitro liver models for high-throughput screening of drugs for their pharmacological and toxicology effects on hepatocytes has remained elusive.

SUMMARY OF THE INVENTION

The present invention features assays for co-culturing primary cells while maintaining key biological activities specific to the primary cells. The invention is based, at least in part, on the discovery that compositions and methods for primary cells in a high-throughput co-culture platform, image analysis for distinguishing cells in co-cultures and assays that are suitable for screening of agents in epithelial cells, such as hepatocytes.

In one aspect, the invention includes a co-culture for high throughput analysis of primary hepatocytes comprising a layer of feeder cells disposed in a well of a microtiter plate, a layer of primary hepatocytes disposed on the feeder cells at a concentration that prevents contact inhibition of the hepatocytes, and an amount of culture media that supports the hepatocytes and maintains at least one hepatocyte biological activity, wherein the amount is optimized to balance oxygen transport and nutrient supply.

In another aspect, the invention includes a method for high throughput detection of primary epithelial cells in co-culture, comprising providing a co-culture present in a microtiter plate, wherein the co-culture comprises feeder cells and primary epithelial cells, acquiring and comparing images of cell nuclei using a high-throughput screening microscope, thereby detecting primary epithelial cells in co-culture.

In yet another aspect, the invention includes a method for detecting primary epithelial cell proliferation or cell death in co-culture, comprising providing a co-culture present in a microtiter plate, wherein the co-culture comprises feeder cells and primary epithelial cells, acquiring and comparing images of cell nuclei at a first and a second time point using a high-throughput screening microscope, and comparing the number of primary epithelial cell nuclei present at the first and second time points, wherein an increase in the number of epithelial cell nuclei present at the second time point detects an increase in epithelial cell proliferation, and detection of a decrease in primary epithelial cell nuclei present at the second time point detects an increase in cell death.

In still yet another aspect, the invention includes a method for detecting an agent that increases primary epithelial cell proliferation, comprising contacting a co-culture present in a microtiter plate with an agent, wherein the co-culture comprises feeder cells and primary epithelial cells, acquiring and comparing images of primary epithelial cell nuclei at a first and a second time point using a high-throughput screening microscope, and detecting an increase in the number of primary epithelial cell nucleic present in the contacted co-culture relative to an untreated co-culture, wherein detection of an increase in the number of primary epithelial cell nucleic present in the contacted co-culture identifies an agent that increases primary epithelial cell proliferation.

In various embodiments of the above aspects or any other aspect of the invention delineated herein, the invention includes the microtiter plate comprising at least 384-wells.

In another embodiment, the hepatocyte biological activity is selected from the group consisting of albumin secretion, liver-specific protein synthesis, bile production, detoxification of compounds, energy metabolism, and cholesterol metabolism.

In some embodiments, the hepatocytes and feeder cells are plated at a ratio of 1:4. In another embodiment, the feeder cells and hepatocytes are of different species. In yet another embodiment, the feeder cells are present as a confluent layer without aggregation. In still yet another embodiment, the feeder cells express a protein selected from the group consisting of Delta-like homolog 1; C-fos-induced growth factor; Ceruloplasmin; Decorin; Interferon regulatory factor 1; 204 interferon-activatable protein; Splicing factor, arginine/serine-rich 3; JKTBP; Autoantigen La; High mobility group box 1; Esk kinase; mouse dihydrofolate reductase gene: 3' end; Pm1 protein; and Rac GTPase-activating protein 1.

In another embodiment, the feeder cells comprise one or more types of non-parenchymal cells, such as fibroblast or fibroblast-derived cells, and hepatic non-parenchymal cells. The hepatic non-parenchymal cells can be selected from the group consisting of Kupffer cells, Ito cells, endothelial cells, stellate cells, cholangiocytes, and hepatic natural killer cells. In yet another embodiment, the cell adhesion substrate is selected from the group consisting of collagen, fibronectin, vitronectin, laminin, entactin, Arg-Gly-Asp (RGD) peptide, Tyr-Ile-Gly-Ser-Arg (YIGSR) peptide, glycosaminoglycans (GAGs), hyaluronic acid (HA), integrins, ICAMs, selectins, cadherin, and cell-surface protein-specific antibodies, or a combination thereof.

In another embodiment, the culture media comprises hydrocortisone.

In some embodiments, invention includes comparing images of cell nuclei comprises comparing nuclear size, shape, intensity, proximity, and texture, thereby distinguishing feeder cells from primary epithelial cells.

In one embodiment, each well of the microtiter plate comprises at least about 10-500 microliters of liquid or at least about 15-145 microliters of liquid.

In another embodiment, the primary epithelial cells comprise hepatocytes.

In yet another embodiment, the invention further includes detecting whether hepatocytes in the microtiter plate retain hepatocyte identity by measuring hepatocyte biological activity. The hepatocyte biological activity is measured using an immunoassay that detects albumin output as a surrogate marker for protein synthesis, using a colorimetric assay that detects urea generation as a surrogate marker for amino acid metabolism function, or by detecting cytochrome P450 activity as a surrogate marker for detoxification.

Another aspect of the invention includes a method for optimizing a co-culture of primary hepatocytes for use in the method described herein, the method comprising plating primary hepatocytes and feeder cells into wells of a microtiter plate at about a 1:4 ratio, wherein each well comprises at least about 10-150 microliters of culture media.

Yet another aspect of the invention includes a method for distinguishing two or more cell types in a co-culture comprising imaging nuclei of the two or more cell types, and comparing nuclear morphology of the nuclei to distinguish the cell types.

In various embodiments of the above aspects or any other aspect of the invention delineated herein, the invention includes the nuclear morphology comprising at least one selected from the group consisting of nuclear size, nuclear shape, nuclear intensity, nuclear proximity, and nuclear texture. In another embodiment, the invention includes producing computer images of the nuclei, such as by automatically calculating a number of nuclei of individual cell types in the co-culture. In another embodiment, the invention includes acquiring two or more images at successive time points, such as by quantifying a change in nuclei numbers of individual cell types in the co-culture.

In another embodiment, the invention includes quantifying nuclei undergoing mitosis, such as by quantifying metaphase and anaphase nuclei.

In another aspect, the invention includes a method for assessing an agent that alters hepatocyte biological activity, comprising contacting a hepatocyte present in the co-culture of any one of claims 1-12 with an agent, and assaying for an alteration in hepatocyte biological activity relative to a control hepatocyte not exposed to the agent, wherein detection of the alteration identifies the agent as altering hepatocyte biological activity.

In yet another aspect, the invention includes a method for assessing the metabolism of a test agent by hepatocytes comprising exposing the co-culture of any one of claims 1-12 to a test agent, and detecting, identifying, and/or quantifying metabolites of the test agent.

In various embodiments of the above aspects or any other aspect of the invention delineated herein, the invention includes the hepatocyte biological activity is proliferation, viability, differentiation, toxicity, or cell death. In another embodiment, the invention further comprises measuring albumin output as a surrogate marker for protein synthesis; measuring urea generation as a surrogate marker for amino acid metabolism function; and/or measuring cytochrome P450 activity as a surrogate marker for detoxification.

The present invention provides a co-culture system and assays compatible with automated high throughput detection and/or quantification of cellular activity in response to agents and/or environmental conditions in epithelial cells. The present invention further provides methods for assessing the effects of agents on epithelial cells and predicting the effect of a test agent on epithelial cells of a subject in vivo. The present invention further provides a method for assessing the metabolism of a test agent by hepatocytes, e.g., by hepatocytes of a particular subject to be treated with the test agent. In preferred embodiments of the various compositions, cultures, and methods disclosed herein, the epithelial cells are hepatocytes, such as human hepatocytes or primary human hepatocytes.

The invention provides a co-culture comprising i) a surface coated by a cell adhesion substrate; ii) a layer of feeder cells disposed on the cell adhesion substrate; and iii) a layer of epithelial cells disposed on the opposite surface of the feeder cells relative to the cell adhesion substrate. The epithelial cells may comprise human epithelial cells or primary human epithelial cells.

In certain embodiments, the feeder cells comprise non-parenchymal cells or cells (such as fibroblasts) expressing one or more proteins selected from Table 1. Non-parenchymal cells may comprise stromal cells or hepatic non-parenchymal cells. Stromal cells may comprise fibroblast or fibroblast-derived cells, such as murine, embryonic, or murine embryonic J2-3T3 fibroblasts. In certain embodiments, hepatic non-parenchymal cells are selected from Kupffer cells, Ito cells, endothelial cells, stellate cells, cholangiocytes (bile duct cells), and hepatic natural killer cells (pit cells).

In certain embodiments, feeder cells are growth-inhibited. In certain embodiments, the co-culture further comprises hydrocortisone.

In certain embodiments, the layer of feeder cells is confluent.

In certain embodiments, the one or more epithelial cells contact the feeder cells.

In certain embodiments, the cell adhesion substrate comprises collagen (such as collagen I), fibronectin, vitronectin, laminin, entactin, Arg-Gly-Asp (RGD) peptide, Tyr-Ile-Gly-Ser-Arg (YIGSR) peptide, glycosaminoglycans (GAGs), hyaluronic acid (HA), integrins, ICAMs, selectins, cadherin, or cell-surface protein-specific antibodies, or a combination thereof.

In certain embodiments, the surface is a surface of a culture well or glass slide.

In certain embodiments, the co-culture is housed in a bioreactor. In certain embodiments, the bioreactor controls gas exchange across the cell populations. In certain embodiments, the bioreactor controls oxygen gradient across the cell populations.

In certain embodiments, the invention provides a multi-well plate comprising a plurality of wells containing a co-culture as described herein, wherein the plate is compatible for use in high-throughput screening of agents, as well as methods of preparing cultures in such plates. In certain embodiments, the multiwell plate contains 96, 384, or more than 384 wells.

In certain embodiments, the invention provides a method of assessing the effect of a test agent on an epithelial cell, such as a hepatocyte, in the co-culture of the invention, e.g., by contacting the epithelial cell with the test agent and assaying for a pharmacological or toxicological effect in the epithelial cells relative to a control epithelial cell not treated with the test agent. The pharmacological or toxicological effect may be proliferation, survival, differentiation, toxicity, or combinations thereof. In certain embodiments, the assay comprises quantifying the number of epithelial cells in the co-culture of the invention by using nuclear morphologies to distinguish an epithelial cell from a feeder cell. In certain embodiments, the assay is selected from measuring albumin synthesis, urea secretion, and cytochrome p450 activity, or combinations thereof.

In certain embodiments, the invention provides a method for predicting the effect of a test agent on epithelial cells, such as hepatocytes, of a subject in vivo, comprising culturing epithelial cells obtained from a subject in the co-culture of the invention, exposing the epithelial cell to the test agent, and assaying for a pharmacological or toxicological effect of the test agent on the epithelial cells relative to control epithelial cells not treated with the test agent. The pharmacological or toxicological effect may be proliferation, survival, differentiation, toxicity, or combinations thereof. In certain embodiments, the assay comprises quantifying the number of epithelial cells in the co-culture by using nuclear morphologies to distinguish an epithelial cell from a feeder cell. In certain embodiments, particularly where the cell is a hepatocyte, the assay is selected from measuring albumin synthesis, urea secretion, and cytochrome p450 activity, or combinations thereof.

In certain embodiments, the invention provides a method for assessing the metabolism of a test agent by epithelial cells, preferably hepatocytes, comprising exposing the co-culture of the invention to a test agent, and determining the effect of the epithelial cells on the test agent. For example, the effect may be measured by detecting, identifying, and/or quantifying metabolites of the test agent, or by determining the half-life of the test agent in the presence of the epithelial cells.

In certain embodiments, the invention provides a method for predicting the metabolism of a test agent by epithelial cells, preferably hepatocytes, of a subject in vivo, comprising culturing epithelial cells obtained from the subject in the co-culture of the invention, exposing the epithelial cells to the test agent, and determining the effect of the epithelial cells on the test agent. For example, the effect may be measured by detecting, identifying, and/or quantifying metabolites of the test agent.

In another aspect, the invention provides a method for producing a co-culture as described above. For example, the method may include:

i) coating a surface with a cell adhesion substrate;
ii) culturing a layer of feeder cells on the cell adhesion substrate; and
iii) overlaying one or more epithelial cells, such as hepatocytes, onto the feeder cells.

The feeder cells and epithelial cells used in the above method can be any of the types of feeder cells and epithelial cells discussed in detail above with respect to the co-culture. The surface may be the surface of a culture well or glass slide, or any other suitable surface. Co-cultures can be contained in a multiwell plate having a 96-, 384-, 1536- or more than 1536-well format.

In certain embodiments, the method comprises culturing the layer of feeder cells to confluence, e.g., prior to introducing epithelial cells. Hydrocortisone or another compound that serves to limit growth and/or proliferation of the feeder cells may be added to the culture, optionally after having cultured the feeder cells to confluence, but preferably before introduction of the epithelial cells. The feeder cells may be cultured for at least for about 24 hours before epithelial cells are added.

Overlaying one or more epithelial cells may comprise dispersing a sparse population of epithelial cells, such as hepatocytes, on a confluent feeder cell layer. The method may further comprise maintaining the epithelial cells for at least 7 days after overlaying the epithelial cells on the feeder cells prior to using the culture for any of the methods discussed herein.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "cell" is meant a structural unit of tissue of a multicellular organism in a living body which is surrounded by a membrane structure which isolates it from the outside and has genetic information and a mechanism for expressing the genetic information. Cells used herein may be naturally-occurring cells or artificially modified cells (e.g., fusion cells, genetically modified cells, etc.).

As used herein, "cellular differentiation" or "differentiation" is the process by which a less specialized cell becomes a more specialized cell type.

By "computer image-based readout" is meant numerical cell measurements derived from a computerized image taken of the co-culture. Platform readiness can be assessed via statistical parameters such as Z'-factor, which reflects the confidence (Z'>0) in the assay readout by detecting both assay signal dynamic range and variation, and is mathematically defined:

$$Z' = 1 - \frac{(3\sigma_{c+} + 3\sigma_{c-})}{|\mu_{c+} - \mu_{c-}|}$$

where "c+"=positive control, "c−"=negative control, "σ"=standard deviation and "μ"=average. Assuming normal distribution, assays with positive Z'-factors can separate 99.8% of the negative and positive control populations (i.e., the two populations, as defined by mean signal+/−3 standard deviations, do not overlap), essentially separating signal from noise.

By "contact inhibition" is meant the cessation of cellular growth, movement, growth processes, or division, upon contact with another cell.

By "culture media" is meant the growth medium with nutrients that is designed to support the growth of cells. The culture media can be specialized for a specific cell type or specific cell process, such as growth and proliferation as opposed to differentiation or maturation of the cells.

By "amount of culture media" is meant the optimal amount of liquid that supports expansion of the cells while allowing gas and nutrient exchange. The amount of culture media is optimized for the cells and the culture format. For example, larger cells in a multi-well format requires more media per cell than smaller cells. Additionally, small multi-well formats, such as 384 wells or smaller, require less media per well than larger multi-well formats, such as a 12 wells or 48 wells.

By "epithelial cell" is meant a cell that lines a body cavity or organ and/or covers an external surface of an organ. Epithelial cells maintain a closed barrier to the external environment and provide the first line of defense against disease or infection. Examples of epithelial cells include, hepatocytes, alveolar cells, skin epithelia, gastrointestinal tract lining, mucus lining, and lining of vessels and capillaries.

By the term "feeder cells" is meant cells that are usually adherent and growth-arrested but viable and bioactive. Feeder cells provide an intact and functional extracellular matrix and secrete matrix-associated factors and cytokines. Feeder cells are typically used to support the growth and survival of a second cell type. Examples of feeder cells include, but are not limited to, non-parenchymal cells, such as fibroblast or fibroblast-derived cells. Exemplary examples for hepatocyte cultures may include, hepatic non-parenchymal cells, such as Kupffer cells, Ito cells, endothelial cells, stellate cells, cholangiocytes (bile duct cells), and hepatic natural killer cells (pit cells).

The term "hepatocyte" as used herein is meant to include hepatocyte-like cells that exhibit some but not all characteristics of mature hepatocytes, as well as mature and fully functional hepatocytes. The cells produced by this method may be as at least as functional as the hepatocytes produced by directed differentiation to date. This technique may, as it is further improved, enable the production of completely fully functional hepatocytes, which have all characteristics of hepatocytes as determined by morphology, marker expression, in vitro and in vivo functional assays.

By "hepatocyte characteristic" is meant a feature or quality that is displayed by hepatocyte cells. Typically, the hepatocyte characteristic is specific to the hepatocyte. Examples of hepatocyte characteristics include, but are not limited to, hepatocyte surface markers, distinct nuclei, polygonal morphology, well-demarcated cell-cell borders, and visible bile canaliculi network.

By "hepatocyte biological activity" is meant an activity or process that is specific to hepatocytes. Examples of hepatic function include, but are not limited to, liver-specific protein synthesis, albumin secretion, bile production, detoxification of compounds, energy (amino acids, fats, sugars etc.) metabolism, and cholesterol metabolism.

By "high throughput detecting" and "high throughput detection" refers to a process that uses a combination of modern robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 864 samples, 1536 samples or more. A typical high throughput screening robot tests up to 100,000 to a few hundred thousand compounds per day. The samples are often in small volumes, such as no more than 1 mL, 500 μl, 200 μl, 100 μl, 50 μl or less.

"High-throughput screening," "high throughput screen" and "HTS" refers to a process that uses high throughput detection. A typical HTS robot tests up to 100,000 to a few hundred thousand compounds per day. The samples are often in small volumes, such as no more than 1 mL, 500 μl, 200 μl, 100 μl, 50 μl or less. Through this process one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

By "high throughput screening microscope" is meant a microscope configured to be self-focusing. Optionally, the high throughput screening microscope is coupled to a barcode reader and robotic arm for automated plate loading. The high-throughput screening microscope has the capacity to view fluorescently labeled samples.

By "liver condition" is meant a disease, disorder, or condition with or affecting the liver. The liver condition affects or disrupts liver function, such as storing and filtering blood, liver-specific protein synthesis, bile production, detoxification of compounds, energy metabolism, and cholesterol metabolism.

By "miniaturized high through-put assay" is meant a small-scale culture format. In an exemplary embodiment, the miniaturized high through-put assay is a multi-well format having at least 384 wells, 864 well, 1534 wells, etc. By "microtiter plate" is meant a small scale culture format comprising. Examples of such multi-well formats include, but are not limited to, 96-well, 384-well, 864-well, 1536-well or greater than 1536-well format.

By "multi-well format" is meant a culture format comprising more than one well. Examples of such multi-well formats include, but are not limited to, 6-well, 12-well, 24-well, 48-well, 96-well, 384-well, 864-well, 1536-well or greater than 1536-well format.

By "non-aggregated" or "without aggregation" is meant distributing the cells as discrete cells with sufficient room to proliferate, not as colonies of cells in a small area.

By "nuclear morphology" is meant the features of nuclei associated with a specific cell type, species, stage of development, diseased status, etc. Nuclear morphology can be assessed by the shape, size, granularity, intensity, proximity, and/or texture of nuclei. Differences in nuclear morphologies can be useful in distinguishing cell types, species, stages of development, or disease status.

By "surrogate marker" is meant a measurement of an activity or biomarker that indicates, reflects or substitutes for another measurement of an activity or biomarker.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "cell adhesion substrate" is meant a molecule or compound that aids in cell adhesion. Examples of cell adhesion substrates include, but are not limited to, extracellular matrix proteins, collagen, fibronectin, vitronectin, laminin, entactin, Arg-Gly-Asp (RGD) peptide, Tyr-Ile-Gly-Ser-Arg (YIGSR) peptide, glycosaminoglycans (GAGs), hyaluronic acid (HA), integrins, ICAMs, selectins, cadherin, and cell-surface protein-specific antibodies, or a combination thereof.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" and "detecting" refers to identifying or measuring the presence, absence or amount of a biological activity or cell.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include, but are not limited to, liver-based metabolic disease, chronic liver failure, acute liver failure, genetic metabolic defect, familial tyrosinemia, cirrhosis, hepatitis, liver abscesses and drug induced liver failure.

By "effective amount" is meant the amount of a required to ameliorate the symptoms of a disease relative to an untreated patient. The effective amount of active compound(s) or cells used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a screening assay and detection method that are useful for the discovery of drugs to induce expansion, differentiation or antagonize processes that induce expansion and/or differentiation of cells, such as liver cells. In addition, the methods of the invention provide a facile means to identify therapies that are safe for use in subjects. In addition, the methods of the invention provide a route for analyzing virtually any number of compounds for effects on a cell described herein with high-volume throughput, high sensitivity, and low complexity.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by inserting certain genes, referred to as reprogramming factors.

As used herein, the term "stem cell" refers to a cell capable of giving rising to at least one type of a more specialized cell. A stem cell has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cell, or somatic stem cell). Any artificially produced cell which can have the above-described abilities (e.g., fusion cells, reprogrammed cells, or the like used herein) may be a stem cell.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, the cells of this invention are purified if they are substantially free of other cells, viral material, or other components. Purity and homogeneity are typically determined using analytical techniques, for example, flow cytometry.

By "surface marker" is meant any protein or carbohydrate found on the surface of a cell that can be detected by immunological staining, flow cytometry, ELISA, or other assays known to those having ordinary skill in the art. The surface marker may also be associated with expression level or activity or alteration in expression or activity that is associated with particular cell type, stage of development, a disease or disorder.

As used herein, "obtaining" as in "obtaining an agent" includes synthesizing, purchasing, isolating, purifying or otherwise acquiring the agent.

By "reduces" is meant a negative alteration of at least 10%, 25%, 50%, 75%, or 100%.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 4A shows that nuclei were visualized with Hoechst stain, and imaged using a high-content screening microscope.

FIG. 4B is an image detailing the differences in nuclear morphologies of Hoechst stained hepatocyte and fibroblast nuclei.

FIG. 4C is an image showing the user interface window to identify and characterize nuclei through a custom image-based proliferation assay. The user interface window of the classification software, CellProfiler Analyst, is shown. It allowed manual classification of randomly presented nuclei and error correction of machine-classified nuclei.

FIG. 4D shows an example of the automated nuclei classification and counting analysis generated by the software.

DETAILED DESCRIPTION OF THE INVENTION

Figure 1A:
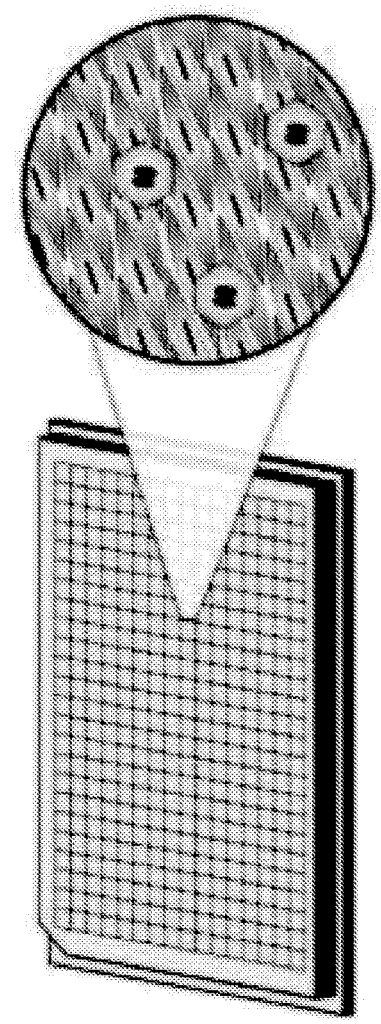
FIG. 1A shows a schematic of a 384-well co-culture platform.

As described below, the present invention features assays for co-culturing primary cells while maintaining key biological activities specific to the primary cells. The invention is based, at least in part, on the discovery that compositions and methods for primary cells in a high-throughput co-culture platform, image analysis for distinguishing cells in co-cultures and assays that are suitable for screening of agents in epithelial cells, such as hepatocytes.

Co-Culture

The present invention includes a co-culture for high throughput analysis of primary hepatocytes comprising a layer of feeder cells disposed in a well of a microtiter plate, a layer of primary hepatocytes disposed on the feeder cells at a concentration that prevents contact inhibition of the hepatocytes, and an amount of culture media that supports the hepatocytes and maintains at least one hepatocyte biological activity, wherein the amount is optimized to balance oxygen transport and nutrient supply The invention includes a co-culture optimized for a multi-well format. The multi-well format includes larger formats, such as 6, 12, 24, 48, and 96 wells. In one embodiment, the feeder cells and hepatocytes are disposed in a microtiter plate. The microtiter plate includes those having at least 384, 864, 1536 wells, or a greater number of wells.

In another embodiment, the concentration of hepatocytes disposed on the feeder cells is at an optimal concentration that prevents contact-inhibition of the hepatocytes. The hepatocytes can be plated at a ratio to the feeder cells of less than about 1:4. In some embodiments, the concentration comprises a ratio of hepatocytes to the feeder cells of less than about 1:2, 1:3, 1:4, 1:5, 1:6, 1:7, 1:8, 1:9, 1:10 or any ratio therebetween.

The co-culture further maintains hepatocyte functions and characteristics of the hepatocytes. In one embodiment, the hepatocytes maintain at least one hepatocyte biological activity throughout co-culturing. Examples of hepatocyte biological activity include, but are not limited to, liver-specific protein synthesis (albumin secretion), bile production, detoxification of compounds, energy (amino acid, fat and sugar) metabolism, and cholesterol metabolism.

In certain embodiments, the co-culture comprises i) a surface coated by a cell adhesion substrate; ii) a layer of feeder cells disposed on the cell adhesion substrate; and iii) a layer of epithelial cells, such as hepatocytes, disposed on the opposite surface of the feeder cells relative to the cell adhesion substrate. The epithelial cells may comprise human epithelial cells, primary human epithelial cells, endothelial-derived epithelial cells, or hepatocytes, including hepatocytes expanded in animals (e.g., as produced in mice, such as cells available from Yecuris Corporation as human hepatocytes) and hepatocytes derived from adult stem cells, embryonic stem cells, or induced pluripotent stem cells such as iHep cells.

In certain embodiments, iHep cells are derived from induced pluripotent stem cells by i) culturing undifferentiated iPS cells on a hydrogel protein matrix; ii) transferring confluent iPS cells to differentiation media; and iii) adding growth factors (Activin A, BMP-4, bFGF, HGF, and OSM).

In certain embodiments, epithelial cells are obtained from a subject with a healthy organ, such as hepatocytes from a healthy liver, while in other embodiments the epithelial cells may be obtained from a subject with a diseased organ, such as hepatocytes, from a disease liver. The epithelial cells may be adult or embryonic.

Feeder cells are important to maintain the quality of the epithelial cells (such as hepatocytes) in the culture. Suitable feeder cells may comprise non-parenchymal cells or cells (such as fibroblasts) expressing a protein selected from Table 1 or Delta-like homolog 1; C-fos-induced growth factor; Ceruloplasmin; Decorin; Interferon regulatory factor 1; 204 interferon-activatable protein; Splicing factor, arginine/serine-rich 3; JKTBP; Autoantigen La; High mobility group box 1; Esk kinase; mouse dihydrofolate reductase gene: 3' end; Pm1 protein; and Rac GTPase-activating protein 1.

TABLE 1

Fibroblast Candidate Genes Whose Expression Profiles Correlate Positively With the Inductive Profile Shown in FIG. 1A

| Accession Number | Description |
|---|---|
| | Cell Surface |
| Z12171 | Delta-like homolog 1 (*Drosophila*) |
| | Secreted |
| X99572 | C-fos-induced growth factor (VEGF-D) |
| U49513 | Small inducible cytokine A9 |
| U49430 | Ceruloplasmin |
| | Extracellular matrix or matrix remodeling |
| X53929 | Decorin |
| | Transcription factors |
| M21065 | Interferon regulatory factor 1 |
| M31419 | 204 interferon-activatable protein |
| | Other |
| X53824 | Splicing factor, arginine/serine-rich 3 |
| AB017020 | Heterogeneous nuclear ribonucleoprotein D-like protein JKTBP |
| L00993 | Autoantigen La (SS-B) |
| U004311 | High mobility group box |
| Z72486 | DNA polymerase delta small subunit (pold2) |
| M86377 | Esk kinase |
| J00388 | Mouse dihydrofolate reductase gene: 3' end |
| X07967 | Pm1 protein |

TABLE 1-continued

Fibroblast Candidate Genes Whose Expression Profiles Correlate
Positively With the Inductive Profile Shown in FIG. 1A

| Accession Number | Description |
| --- | --- |
| AW122347 (EST) | Rac GTPase-activating protein 1 |
| AA655369 (EST) | Translocase of inner mitochondrial membrane 8 homolog a, yeast |

NOTE.
Unknown function EST accession numbers; AI037577, AI846197, AI841894, AI606951, AA940036, AI746846, AI551087, AA222883, AI848479.

In certain embodiments, wherein feeder cells comprise non-parenchymal cells, non-parenchymal cells may comprise stromal cells or hepatic non-parenchymal cells. In certain embodiments, wherein non-parenchymal cells comprise stromal cells, stromal cells may comprise fibroblast or fibroblast-derived cells. In certain embodiments, wherein stromal cells comprise fibroblast or fibroblast-derived cells, fibroblast or fibroblast-derived cells may be murine and/or embryonic. In a preferred embodiment, the feeder cells are murine embryonic J2-3T3 fibroblasts.

In certain embodiments, wherein non-parenchymal cells comprise hepatic non-parenchymal cells, hepatic non-parenchymal cells are selected from Kupffer cells, Ito cells, endothelial cells, stellate cells, cholangiocytes (bile duct cells), and hepatic natural killer cells (pit cells).

In some embodiment, the feeder cells have different morphologies and/or characteristics from the hepatocytes. For example, the feeder cells may have different nuclear morphology, be of a different species (e.g., mouse vs. human), and a different cell type (non-parenchymal vs epithelial cells).

In certain embodiments, feeder cells are growth-inhibited, which helps avoid overgrowth of the feeder cells and maintain confluent feeder cells in a single layer. In one embodiment, the feeder cells are present as a confluent layer without aggregation. Feeder cells can be growth-inhibited by irradiation, treatment with mitomycin c, high-temperature treatment, chemical fixation, treatment with steroids such as hydrocortisone or dexamethasone, or any other suitable means that reduces their proliferative capacity.

In certain embodiments, the co-culture further comprises hydrocortisone, which also helps to avoid over-proliferation of the feeder cells. Feeder cells growth-inhibited by hydrocortisone appear to support epithelial cells, such as hepatocytes, in the co-culture for an extended period of time, for example for at least 9 days in culture.

In certain embodiments, the layer of feeder cells is confluent.

In certain embodiments, cell adhesion substrate may be selected from collagen type I, collagen type II, collagen type IV, fibronectin, vitronectin, laminin, entactin, Arg-Gly-Asp (RGD) peptide, Tyr-Ile-Gly-Ser-Arg (YIGSR) peptide, glycosaminoglycans (GAGs), hyaluronic acid (HA), integrins, ICAMs, selectins, cadherin, and cell-surface protein-specific antibodies, or a combination thereof. Cell adhesion substrates may also be selected from collagen III, collagen IV, collagen V, laminin á2, tenascin-R, chondroitin sulfate proteoglycans, aggrecan, elastin, keratin, mucin, superfibronectin, F-spondin, nidogen-2, heparan sulfate proteoglycan (perlecan), biglycan, decorin, galectin-1, galectin-3, galectin-3c, galectin-4, galectin-8, thrombospondin-4, osteopontin, osteonectin, testican 1, testican 2, fibrin, tenascin-C, nidogen-1, agrin, hyaluronan, and brevican as disclosed in Reticker-Flynn Nature Communications July 2012; DOI: 10.1038/ncomms2128, which is hereby incorporated by reference in its entirety. Cell adhesion substrates may also be selected from nucleic acids, nucleic acid binding partners, receptors, antibodies, enzymes, carbohydrates, oligosaccharides, polysaccharides, cells, cell aggregates, cell components, lipids, arrays of ligands (e.g., non-protein ligands), liposomes, microorganisms, e.g., bacteria, viruses, and the like, as disclosed in greater detail in WO2002/04113, which is hereby incorporated by reference in its entirety. In a preferred embodiment, the cell adhesion substrate is collagen I. Coating the surface with a cell adhesion substrate fosters secure cell attachment, important for maintenance of co-culture and screening purposes.

In certain embodiments, the surface of the co-culture consists of polymeric materials, glass, semiconductors, or metals that may be arranged in a variety of configurations, for example a polymeric culture well or glass slide, or any other suitable combinations thereof. As is well known in the art, culture wells may be in a single, multi-well format or microtiter plate, Multi-well format includes 6-well, 12-well, 24-well, 48-well, 96-well, 384-well, 864-well, 1536-well or greater than 1536-well format. Microtiter plates include 96-well, 384-well, 864-well, 1536-well or greater than 1536-well format.

In certain embodiments, one or more epithelial cells contact the feeder cells.

In certain embodiments, the co-culture is housed in a bioreactor, such as a bioreactor disclosed in WO 2004/076647, which is hereby incorporated by reference in its entirety. In certain embodiments wherein the co-culture is housed in a bioreactor, the bioreactor controls gas exchange across the cell populations. In certain embodiments wherein the bioreactor controls gas exchange across the cell populations, the bioreactor controls oxygen gradient across the cell populations.

In certain embodiments, the co-cultures contains an epithelial cell, such as a hepatocyte, enabling single cell analysis. In other embodiments, the co-culture contains more than one epithelial cell, enabling multicell analysis.

In certain embodiments, the invention provides a method for producing the co-culture of the present invention, the method comprising i) coating a surface with a cell adhesion substrate; ii) culturing a layer of feeder cells on the cell adhesion substrate; and iii) overlaying one or more epithelial cells, such as hepatocytes, onto the feeder cells.

In certain embodiments, the surface of the co-culture consists of polymeric materials, glass, semiconductors, or metals that may be arranged in a variety of configurations, for example a polymeric culture well or glass slide, or any other suitable combinations thereof. As is well known in the art, culture wells may be in a single or multiwell format, such as a 96-well, 384-well, 1536-well or greater than 1536-well plate.

In certain embodiments, cell adhesion substrate may be selected from collagen type I, collagen type II, collagen type IV, fibronectin, vitronectin, laminin, entactin, Arg-Gly-Asp (RGD) peptide, Tyr-Ile-Gly-Ser-Arg (YIGSR) peptide, glycosaminoglycans (GAGs), hyaluronic acid (HA), integrins, ICAMs, selectins, cadherin, and cell-surface protein-specific antibodies, or a combination thereof. Cell adhesion substrates may also be selected from collagen III, collagen IV, collagen V, laminin á2, tenascin-R, chondroitin sulfate proteoglycans, aggrecan, elastin, keratin, mucin, superfibronectin, F-spondin, nidogen-2, heparan sulfate proteoglycan (perlecan), biglycan, decorin, galectin-1, galectin-3, galectin-3c, galectin-4, galectin-8, thrombospondin-4, osteopontin, osteonectin, testican 1, testican 2, fibrin, tenascin-C, nidogen-1, agrin, hyaluronan, and brevican as disclosed in Reticker-Flynn Nature Communications July 2012 DOI: 10.1038/ncomms2128, which is hereby incorporated by reference in its entirety. Cell adhesion substrates may also be selected from nucleic acids, nucleic acid binding partners, receptors, antibodies, enzymes, carbohydrates, oligosaccharides, polysaccharides, cells, cell aggregates, cell components, lipids, arrays of ligands (e.g., non-protein ligands), liposomes, microorganisms, e.g., bacteria, viruses, and the like, as disclosed in greater detail in WO2002/04113, which is hereby incorporated by reference in its entirety. In preferred embodiments, the cell adhesion substrate is collagen I, optionally presented as a coating of collagen, which may be adsorbed onto or otherwise disposed on the surface. Coating the surface with a cell adhesion substrate, e.g., by adsorbing collagen onto the surface, such as by incubating the surface in a solution of collagen, allows for secure cell attachment, important for maintenance of co-culture and screening purposes.

Methods of Co-Culturing

The present invention also includes, in one aspect, a method for high throughput detection of primary epithelial cells in co-culture, comprising providing a co-culture present in a microtiter plate, wherein the co-culture comprises feeder cells and primary epithelial cells, acquiring and comparing images of cell nuclei using a high-throughput screening microscope, thereby detecting primary epithelial cells in co-culture.

In another aspect, the invention includes a method for detecting primary epithelial cell proliferation or cell death in co-culture, comprising providing a co-culture present in a microtiter plate, wherein the co-culture comprises feeder cells and primary epithelial cells, acquiring and comparing images of cell nuclei at a first and a second time point using a high-throughput screening microscope, and comparing the number of primary epithelial cell nuclei present at the first and second time points, wherein an increase in the number of epithelial cell nuclei present at the second time point detects an increase in epithelial cell proliferation, and detection of a decrease in primary epithelial cell nuclei present at the second time point detects an increase in cell death.

In yet another aspect, the invention includes a method for detecting an agent that increases primary epithelial cell proliferation, comprising contacting a co-culture present in a microtiter plate with an agent, wherein the co-culture comprises feeder cells and primary epithelial cells, acquiring and comparing images of primary epithelial cell nuclei at a first and a second time point using a high-throughput screening microscope; and detecting an increase in the number of primary epithelial cell nucleic present in the contacted co-culture relative to an untreated co-culture, wherein detection of an increase in the number of primary epithelial cell nucleic present in the contacted co-culture identifies an agent that increases primary epithelial cell proliferation.

The method for detecting is further optimized with each well of the microtiter plate comprising at least about 10-500 microliters of liquid. In some embodiment, each well of the microtiter plate comprises at least about 10, 15, 20, 25, 30, 35, 40, 45, 50, 55, 60, 65, 70, 75, 80, 85, 90, 95, 100, 150, 200, 250, 300, 350, 400, 450, 500 microliters, or more of liquid. In one embodiment, each well of the microtiter plate comprises at least about 15-145 microliters of liquid.

To distinguish feeder cells from primary epithelial cells, nuclear size, shape, intensity, proximity, and texture of the cell nuclei are compared. Different cell types also can be distinguished from one another, such as the primary epithelial cells can be distinguished from the feeder cells. In another embodiment, the feeder cells and primary epithelial cells are from different species.

The method can further comprise detecting whether hepatocytes in the microtiter plate retain hepatocyte identity by measuring hepatocyte biological activity. The hepatocyte biological activity can be measured using an immunoassay that detects albumin output as a surrogate marker for protein synthesis, using a colorimetric assay that detects urea generation as a surrogate marker for amino acid metabolism function and/or detecting cytochrome P450 activity as a surrogate marker for detoxification.

Another aspect of the invention includes a method for optimizing a co-culture of primary hepatocytes for use in any method described herein comprising plating primary hepatocytes and feeder cells into wells of a microtiter plate at about a 1:4 ratio, wherein each well comprises at least about 10-150 microliters of culture media.

The method for detecting primary epithelial cells in the co-culture provides for plating feeder cells onto the cell adhesion substrate coated surface. Feeder cells are important to maintain the quality of the epithelial cells in the culture. Suitable feeder cells may comprise non-parenchymal cells or cells (such as fibroblasts) expressing a protein selected Delta-like homolog 1; C-fos-induced growth factor; Ceruloplasmin; Decorin; Interferon regulatory factor 1; 204 interferon-activatable protein; Splicing factor, arginine/serine-rich 3; JKTBP; Autoantigen La; High mobility group box 1; Esk kinase; mouse dihydrofolate reductase gene: 3' end; Pm1 protein; and Rac GTPase-activating protein 1 or from Table 1.

In certain embodiments, wherein feeder cells comprise non-parenchymal cells, non-parenchymal cells may comprise stromal cells or hepatic non-parenchymal cells. In certain embodiments, wherein non-parenchymal cells comprise stromal cells, stromal cells may comprise fibroblast or fibroblast-derived cells. In certain embodiments, wherein stromal cells comprise fibroblast or fibroblast-derived cells, fibroblast or fibroblast-derived cells may be murine and/or embryonic. In a preferred embodiment, the feeder cells are murine embryonic J2-3T3 fibroblasts. In certain embodiments, wherein non-parenchymal cells comprise hepatic non-parenchymal cells, hepatic non-parenchymal cells are selected from Kupffer cells, Ito cells, endothelial cells, stellate cells, cholangiocytes (bile duct cells), and hepatic natural killer cells (pit cells).

In certain embodiments, feeder cells are growth-inhibited, which helps avoid overgrowth of the feeder cells and maintain confluent feeder cells in a single layer. Feeder cells are plated onto the cell adhesion substrate coated surface and allowed to reach confluence, when their growth becomes contact inhibited. For example, J2-3T3 fibroblasts plated at 8,000 cells/well in a 384-well plate reach confluence 48 hours later under typical culture conditions.

In certain embodiments, the co-culture further comprises hydrocortisone added to the co-culture medium, which also helps to avoid over-proliferation of the feeder cells. Feeder cells growth-inhibited by hydrocortisone appear to support epithelial cells, such as hepatocytes, in the co-culture for an extended period of time, for example for at least 9 days.

The method for detecting primary epithelial cells in the co-culture provides for plating one or more epithelial cells, such as hepatocytes, onto feeder cells, e.g., such that the epithelial cells contact the feeder cells. In certain embodiments, a sparse population of epithelial cells is co-cultivated on a confluent feeder cell layer. For example, primary human hepatocytes can be plated onto a confluent layer of J2-3T3 fibroblasts on Day 0 at a density below 5,000 cells/well or even below 3,000 cells/well, e.g., about 2,000 cells/well, in a 384-well plate, or at a correspondingly low density based on the surface area of the well in plates of other sizes. The co-culture can then be maintained under standard conditions with daily replacement of medium. This design provides surface area for cell expansion and stabilizes phenotypic functions in vitro.

The epithelial cells may comprise human epithelial cells, primary human epithelial cells, endothelial-derived epithelial cells, or hepatocytes, including hepatocytes expanded in animals (e.g., as produced in mice, such as human hepatocytes available from Yecuris Corporation) and hepatocytes derived from adult stem cells, embryonic stem cells, or induced pluripotent stem cells such as iHep cells. In certain embodiments, iHep cells are derived from induced pluripotent stem cells by i) culturing undifferentiated iPS cells on a hydrogel protein matrix; ii) transferring confluent iPS cells to differentiation media; and iii) adding growth factors (Activin A, BMP-4, bFGF, HGF, and OSM). In certain embodiments, epithelial cells are obtained from a subject with a healthy organ, such as hepatocytes from a healthy liver, while in other embodiments the epithelial cells may be obtained from a subject with a diseased organ, such as hepatocytes from a disease liver. The epithelial cells may be adult or embryonic. In preferred embodiments of the foregoing, the epithelial cells are hepatocytes, e.g., obtained from a liver.

Cell Imaging

The present invention includes, in one aspect, a method for distinguishing two or more cell types in a co-culture comprising imaging nuclei of the two or more cell types, and comparing nuclear morphology of the nuclei to distinguish the cell types. A key feature of the assay is the ability to distinguish the individual cell types present in the co-culture based on nuclear morphology. The nuclear morphology can include nuclear size, shape, intensity, proximity, and texture of the nuclei.

In one embodiment, the invention includes producing computer images of the nuclei. The produced computer images can be analyzed to calculate the number of nuclei of individual cell types. This may be achieved by producing computer images and automatically calculating a number of nuclei of individual cell types in the co-culture.

Multiple images of the nuclei can also be acquired. Imaging nuclei can include acquiring two or more images at successive time points. The successive time points can be seconds, minutes, hours, days or weeks apart from one another.

In another embodiment, the invention includes comparing nuclear morphology by quantifying a change in nuclei numbers of individual cell types in the co-culture. Comparing nuclear morphology can also include quantifying nuclei undergoing mitosis, including metaphase and anaphase nuclei.

The imaging assay is readily adapted for microscale architectures, such as microtiter plates having at least 384-wells or more. The co-culture is also compatible with automated high-throughput screening platforms to detect and/or quantify cellular activity in response to agents and/or environmental conditions. For example, the initial density of epithelial cells can be low enough to enable proliferative responses to be assessed in the co-culture. In one embodiment, the epithelial cells are disposed on the feeder cells at a ratio of less than about 1:3.

Although these advantages can be very helpful in a variety of situations, culture survival is typically shorter than seen using co-planar systems where the feeder cells surround pockets of hepatocytes. However, such co-planar culture systems may limit proliferative expansion due to contact inhibition and therefore are less well suited to proliferation studies. Platform readiness for HTS was assessed via statistical parameters such as z'-factor, which reflects both assay signal dynamic range and variation, and is mathematically defined:

$$Z' = 1 - \frac{(3\sigma_{c+} + 3\sigma_{c-})}{|\mu_{c+} - \mu_{c-}|}$$

where "c+"=positive control, "c−"=negative control, "σ"=standard deviation and "μ"=average. Assuming normal distribution, assays with positive Z'-factors can separate 99.8% of the negative and positive control populations (i.e., the two populations, as defined by mean signal+/−3 standard deviations, do not overlap), essentially separating signal from noise.

In certain embodiments, the assay measures epithelial proliferation by quantifying epithelial nuclei, using nuclear morphologies to distinguish epithelial cells from co-existing feeder cells of a second cell type. For example, hepatic cell nuclei were uniform in texture while fibroblast nuclei were punctate. Nuclear stains can also be used to enhance visualization and imaging of morphological characteristics. In certain embodiments, image acquisition is further facilitated by typical flattening-out phenomena experienced by cells maintained in culture. In certain embodiments, cells in the feeder layer and in the epithelial layer of the co-culture exist in the same focal plane, allowing simultaneous imaging of both layers without the need for refocusing the detector.

In certain embodiments, a customized, automated, high-content imaging protocol is used to acquire and analyze images. In certain embodiments, automated image analyses utilize machine learning algorithms to classify nuclei types and tabulate epithelial nuclei numbers. Assay validation data show that this image-based readout can confidently (z'>0) detect doublings in hepatic nuclei numbers with low variance (CV<20%) and good reproducibility for accurate proliferation measurements. In certain embodiments, the number of nuclei in the process of mitosis (i.e., undergoing metaphase and anaphase) can also be identified and quantified. In certain embodiments, selective labeling of one population with lipophilic dyes (i.e., carboxyfluorescein diacetate), nuclear stains (i.e., DAPI and Hoechst), or tagged proteins (i.e., GFP-tagged protein) can be used to distinguish cells in a population of interest from un-labeled cells.

Screening Assays

The present invention also includes assays suitable for high-throughput screening of agents in epithelial cells, such as hepatocytes. The co-culture can be used to test the effects of agents on epithelial cells, including predicting the effect of a test agent on epithelial cells of a particular subject. The present invention further provides a method for assessing the metabolism of a test agent by epithelial cells, including epithelial cells of a particular subject.

The co-culture can be used to screen for agents (such as solvents, small molecule drugs, peptides, and polynucleotides) or environmental conditions (such as culture conditions or manipulation) that affect the characteristics of cells. Two or more drugs can be tested in combination (by exposing to the cells either simultaneously or sequentially), to detect possible drug-drug interactions and/or rescue effects (e.g., by testing a toxin and a potential anti-toxin). Drug(s) and environmental condition(s) can be tested in combination (by treating the cells with a drug either simultaneously or sequentially relative to an environmental condition), to detect possible drug-environment interaction effects. Use of the co-culture for screening purposes further comprises assays of cellular activity that include imaging and biochemical read-outs.

In certain embodiments, the assay is selected in a manner appropriate to the cell type and agent and/or environmental factor being studied as disclose in WO 2002/04113, which is hereby incorporated by reference in its entirely. For example, changes in cell morphology may be assayed by standard light, or electron microscopy. Alternatively, the effects of treatments or compounds potentially affecting the expression of cell surface proteins may be assayed by exposing the cells to either fluorescently labeled ligands of the proteins or antibodies to the proteins and then measuring the fluorescent emissions associated with each cell on the plate. As another example, the effects of treatments or compounds which potentially alter the pH or levels of various ions within cells may be assayed using various dyes which change in color at determined pH values or in the presence of particular ions. The use of such dyes is well known in the art. For cells which have been transformed or transfected with a genetic marker, such as the β-galactosidase, alkaline phosphatase, or luciferase genes, the effects of treatments or compounds may be assessed by assays for expression of that marker. In particular, the marker may be chosen so as to cause spectrophotometrically assayable changes associated with its expression.

Particular screening applications of this invention relate to the testing of pharmaceutical compounds in drug research. The reader is referred generally to the standard textbook *In Vitro Methods in Pharmaceutical Research*, Academic Press, 1997, and U.S. Pat. No. 5,030,015. In certain aspects of this invention, the co-culture of the invention is used to grow and differentiate hepatocytes to play the role of test cells for standard drug screening and toxicity assays, as have been previously performed on hepatocyte cell lines or primary hepatocytes in short-term culture. Assessment of the activity of candidate pharmaceutical compounds generally involves combining the hepatocytes with the candidate compound, determining any change in the morphology, marker phenotype, or metabolic activity of the cells that is attributable to the candidate compound (compared with untreated cells or cells treated with an inert compound), and then correlating the effect of the candidate compound with the observed change. The screening may be done because the candidate compound is designed to have a pharmacological effect on liver cells, or because a candidate compound designed to have effects elsewhere may have unintended hepatic side effects. Alternatively, libraries can be screened without any predetermined expectations in hopes of identifying compounds with desired effects.

In some embodiments, the co-culture of the invention is used to screen pharmaceutical compounds for potential cytotoxicity, such as hepatotoxicity (Castell et al., In: *In Vitro Methods in Pharmaceutical Research*, Academic Press, 375-410, 1997. *Cell Encapsulation Technology and Therapeutics*, Kuhtreiber et al. eds., Birkhauser, Boston, Mass., 1999). Cytotoxicity can be determined in the first instance by the effect on cell viability, morphology, and leakage of enzymes into the culture medium. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

In some embodiments, more detailed analysis is conducted to determine whether the pharmaceutical compounds affect hepatic cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al., *Anal. Biochem.*, 236:296, 1996 describes a microassay for measuring glycogen, which can be used to measure the effect of pharmaceutical compounds on hepatocyte gluconeogenesis.

Other methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of alpha-glutathione s-transferase; ATP, ADP, and AMP metabolism; intracellular $K+$ and $Ca2+$ concentrations; the release of nuclear matrix proteins or oligonucleosomes; and induction of apoptosis (indicated by cell rounding, condensation of chromatin, and nuclear fragmentation). DNA synthesis can be measured as $[^3H]$-thymidine or BrdU incorporation. Effects of a drug on DNA synthesis or structure can be determined by measuring DNA synthesis or repair. $[^3H]$-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to Vickers in *In Vitro Methods in Pharmaceutical Research*, Academic Press, 375-410, 1997 for further elaboration.

In certain embodiments, the invention includes a method for assessing an agent that alters hepatocyte biological activity, comprising contacting a hepatocyte present in the co-culture as described herein with an agent, and assaying for an alteration in hepatocyte biological activity relative to a control hepatocyte not exposed to the agent, wherein detection of the alteration identifies the agent as altering hepatocyte biological activity. In certain embodiments, the hepatocyte biological activity is selected from proliferation, survival, differentiation, and toxicity, or combinations thereof. In certain embodiments, the assay comprises measuring albumin output as a surrogate marker for protein synthesis; measuring urea generation as a surrogate marker for amino acid metabolism function; and/or measuring cytochrome P450 activity as a surrogate marker for detoxification.

In certain embodiments, the invention provides a method for predicting the effect of a test agent on epithelial cells, such as hepatocytes, of a subject in vivo, comprising culturing epithelial cells obtained from a subject in the co-culture of the invention, exposing the epithelial cells to the test agent, and assaying for a pharmacological or toxicological effect of the test agent on the epithelial cells relative to control epithelial cells not treated with the test agent. In certain embodiments, a pharmacological or toxicological effect is selected from proliferation, survival, differentiation, and toxicity, or combinations thereof. In certain embodiments, the assay comprises quantifying the number of epithelial cells in the co-culture by using nuclear morphologies to distinguish an epithelial cell from a feeder cell. In certain embodiments, the assay is selected from measuring albumin synthesis, urea secretion, and cytochrome p450 activity, or combinations thereof.

In certain embodiments, the invention provides a method for assessing the metabolism of a test agent by epithelial cells, preferably hepatocytes, comprising exposing the co-culture of the invention to a test agent, and determining the effect of the epithelial cells on the test agent. For example, the effect may be measured by detecting, identifying, and/or quantifying metabolites of the test agent.

In certain embodiments, the invention provides a method for predicting the metabolism of a test agent by epithelial cells, preferably hepatocytes, of a subject, comprising culturing epithelial cells obtained from a subject in the co-culture of the invention, exposing the epithelial cells to the test agent, and determining the effect of the epithelial cells on the test agent. For example, the effect may be measured by detecting, identifying, and/or quantifying metabolites of the test agent.

Additional uses of the co-culture of the invention include, but are not limited to, maintenance and expansion of epithelial cells, such as hepatocytes, for their use in transplantation or implantation in vivo; screening cytotoxic compounds, carcinogens, mutagens, growth/regulatory factors, pharmaceutical compounds, etc., in vitro; elucidating the mechanism of liver diseases and infections; studying the mechanism by which drugs and/or growth factors operate; diagnosing and monitoring liver disease in a patient; gene therapy; and the production of biologically active products, to name but a few.

Additional further uses of the co-culture of the invention include, but are not limited to, its use in research e.g., to elucidate cellular growth mechanisms leading to the identification of novel targets for cancer therapies, to elucidate mechanisms involved in cell fate determination leading to new strategies for cellular reprogramming, and to generate genotype-specific cells for disease modeling, including the generation of new therapies customized to different genotypes. Such customization can reduce adverse drug effects and help identify therapies appropriate to the patient's genotype.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Primary Human Hepatocytes Co-Culture Platform Design

During the initial testing of eight different donors of cryopreserved human hepatocytes, three were non-plateable, thus incompatible with phenotypic screening. While the remaining five donors all yielded hepatocytes that adhered to rigid collagen in culture, one donor was too young (0.1 years) to exhibit a full repertoire of mature hepatocyte functions while another two donors had poor functions at baseline. Ultimately, donor GHA, who was a one-year-old Caucasian female with a cause of death of dry drowning, was chosen. GHA hepatocytes attached well to rigid collagen and demonstrated good synthetic, detoxification and metabolic functions.

TABLE 2

Donors of cryopreserved primary human hepatocytes

| Donor | Age | Plate-able? | Function |
|---|---|---|---|
| HU0845 | 47 yrs | No | N/A |
| HU4122 | 19 yrs | No | N/A |
| HU4088 | 2 yrs | No | N/A |
| HU4100 | 40 yrs | Yes | N/A |
| KQG | 38 yrs | Yes | Low |
| SCT | 38 yrs | Yes | Low |
| RQO | 0.1 yrs | Yes | Too young |
| GHA (donor a) | 1 yr | Yes | Good |

Eight different donor lots were tested for suitability for high-throughput screening through examination of plateability and baseline functions such as albumin secretion, urea production and cytochrome P450 activity.

To maintain primary human hepatocytes in culture, they were co-cultivated with murine embryonic J2-3T3 fibroblasts, which have been shown to transiently stabilize hepatocytes in vitro. This co-culture effect is mediated by heterotypic cell-cell contact between primary hepatocytes and stromal cells as well as continuous stimulation with stromal-derived, short-range signaling molecules.

There exist multiple configurations of co-cultures of primary hepatocytes and J2-3T3 fibroblasts, with varying degrees of architectural organization. The simplest implementation consists of a co-planar distribution of randomly mixed hepatocytes and J2-3T3 fibroblasts on a matrix of rigid collagen type I. More sophisticated designs comprise the application of semiconductor-driven microtechnology to organize primary hepatocytes into in vitro colonies of empirically optimized island sizes, subsequently surrounded by J2-3T3 fibroblasts; this particular configuration is termed micro-patterned co-culture (MPCC). All configurations of hepatocyte-J2 co-cultures were found to maintain primary human hepatocyte functions in vitro for at least 9 days, but none recapitulates their innate potential for substantial proliferation.

In general, increased architectural organization of cells in culture leads to longer-term stabilization of hepatocyte functions, with MPCC being the most optimal configuration, enabling maintenance of hepatocyte functions in vitro for 4-6 weeks. However, while the packing of hepatocytes onto pockets of circular islands tightly surrounded by J2-3T3 fibroblasts maximizes the homotypic cell-cell interactions that enhance long-term hepatocyte survival and function, the confluent cell-cell contact may prevent expansion of any cell type whose proliferation is normally contact-inhibited. Additionally, MPCCs are difficult to miniaturize beyond 96-well platforms and in any case, such prolonged periods of hepatocyte functions are neither necessary nor practical for most whole-cell screens.

Figure 1B:
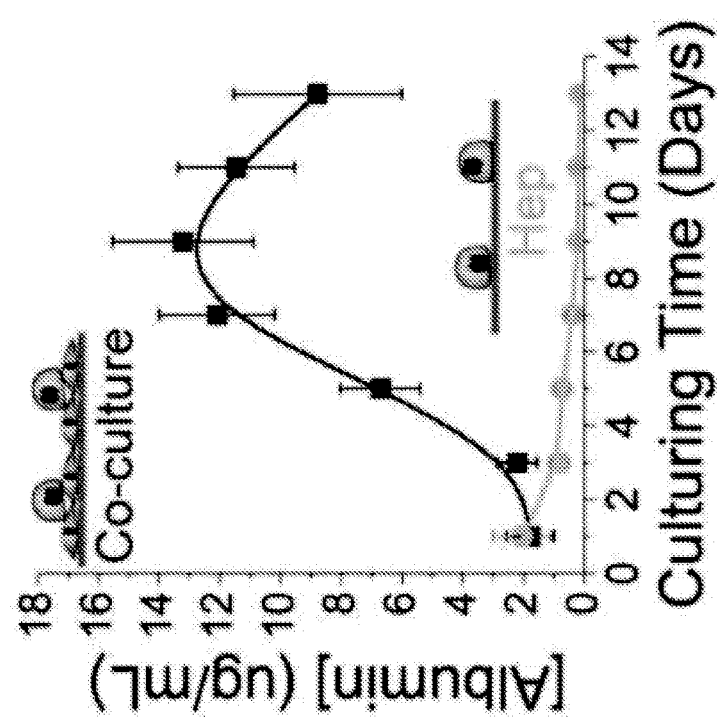
FIG. 1B is a graph showing fibroblast-mediated hepatocyte stabilization for at least 9 days. Line graph shows representative rate of albumin secretion in screening co-cultures and hepatocyte-only cultures (green) over time. All data presented mean±standard deviation.

The high-throughput liver platform was designed to assume a feeder layer co-culture configuration in order to provide both time and space for hepatocyte expansion. The platform contained a sparse population of hepatocytes on top of a confluent layer of J2-3T3s within 384-well plates (FIG. 1A). This design enabled fibroblast-mediated hepatocyte stabilization for at least 9 days (FIG. 1B) without hepatocyte crowding and was amenable to 384-well and smaller formats.

Figure 2:
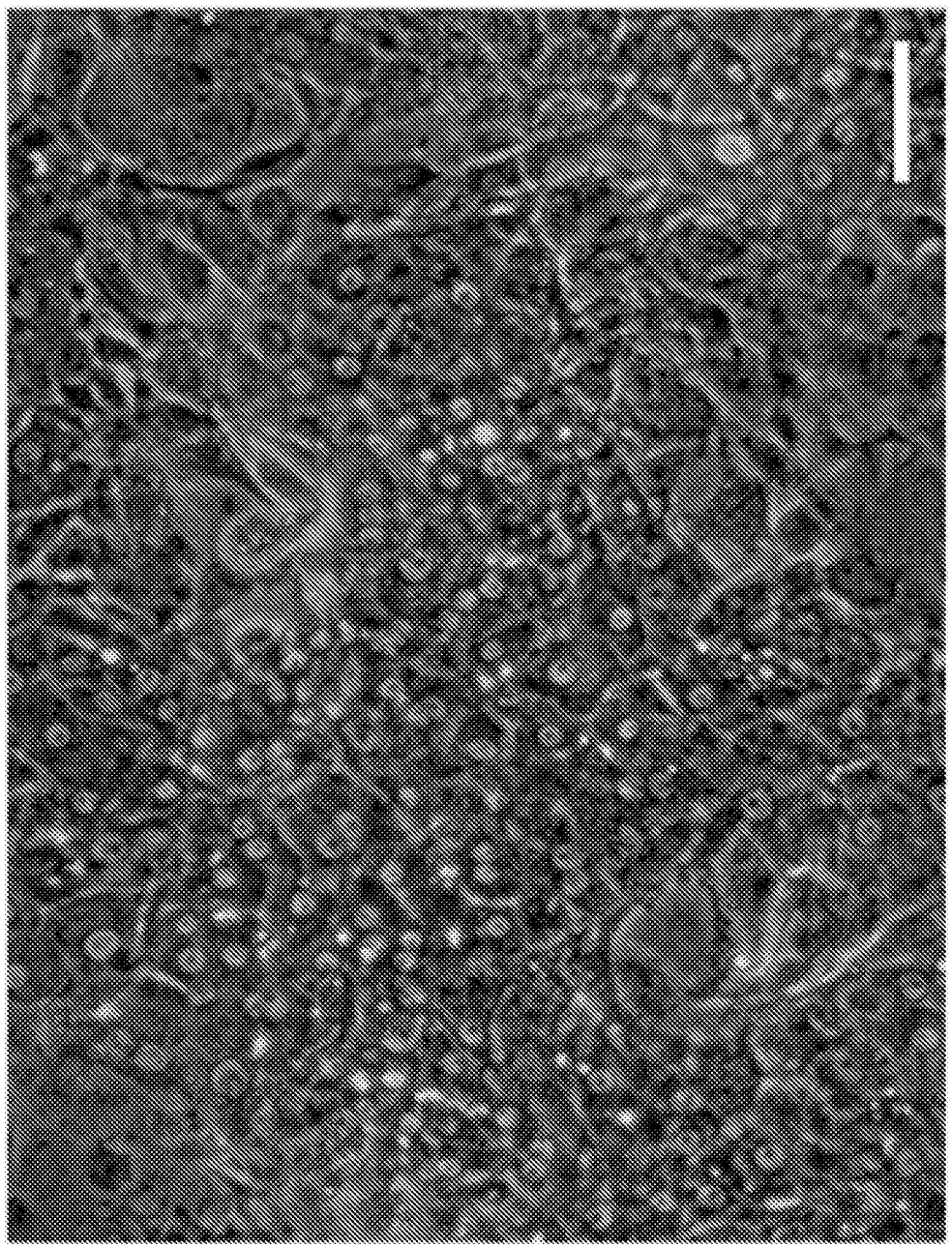
FIG. 2 shows cryopreserved primary human hepatocytes were maintained in vitro through co-cultivation upon a feeder layer of J2-3T3 fibroblasts in 384-well formats. Phase contrast imaging shows morphology of feeder-layer co-cultures (scale bar=100 um).

The number of fibroblasts per well was empirically optimized to 8,000 cells/well in order to establish a confluent feeder layer without contraction and aggregation of overcrowded J2-3T3 fibroblasts. The number of hepatocytes per well was empirically optimized to 2,000 cells/well, minimizing the number of hepatocytes in culture to allow room for expansion while balancing the need for sufficient albumin output detectable via ELISA (FIG. 2).

Similarly, the amount of media used per well was empirically optimized to balance opposing needs of oxygen transport and nutrient supply—too much media presented a transport barrier for gas diffusion, causing observable steatosis in cultured hepatocytes; too little media caused nutrient deprivation. There was an additional restriction that all fluids handled robotically must be dispensed in volumes that are multiples of 10 µl; while the robots can be programmed to dispense in single microliter gradients, only multiples of 10 µl offered sufficient accuracy. All cells were robotically seeded at the lowest possible speed setting in order to minimize physical stresses. During pilot testing, it was observed that fibroblasts had difficulty remaining attached to plain tissue culture plastic in 384-well formats, thus a matrix coating of Collagen type I was added at a concentration of 100 ug/mL. To assess cell fates in this platform, two separate high-throughput readouts were developed: an image-based proliferation assay and three biochemical functional assays.

Example 2

Co-Culture Proliferation Assay

Conventional approaches of co-cultivation of hepatocytes with J2-3T3 fibroblasts allows long-term maintenance of primary human hepatocytes in culture but renders the measurement of hepatocyte proliferation challenging. The co-existence of two different cell types in each well requires a proliferation assay that is specific to hepatocytes. However, all existing measurements of cellular proliferation and number, such as Alamar Blue, Cell Titer Glow and cell cycle stains including Ki67, BrdU and PNA, all reflect the proliferation state of the whole well, which allows behavior of the more populous J2-3T3 fibroblasts to mask moderate hepatocyte expansions in culture. Therefore, a custom image-based readout was developed to specifically measure hepatocyte proliferation in the high-throughput liver platform.

Figure 3:
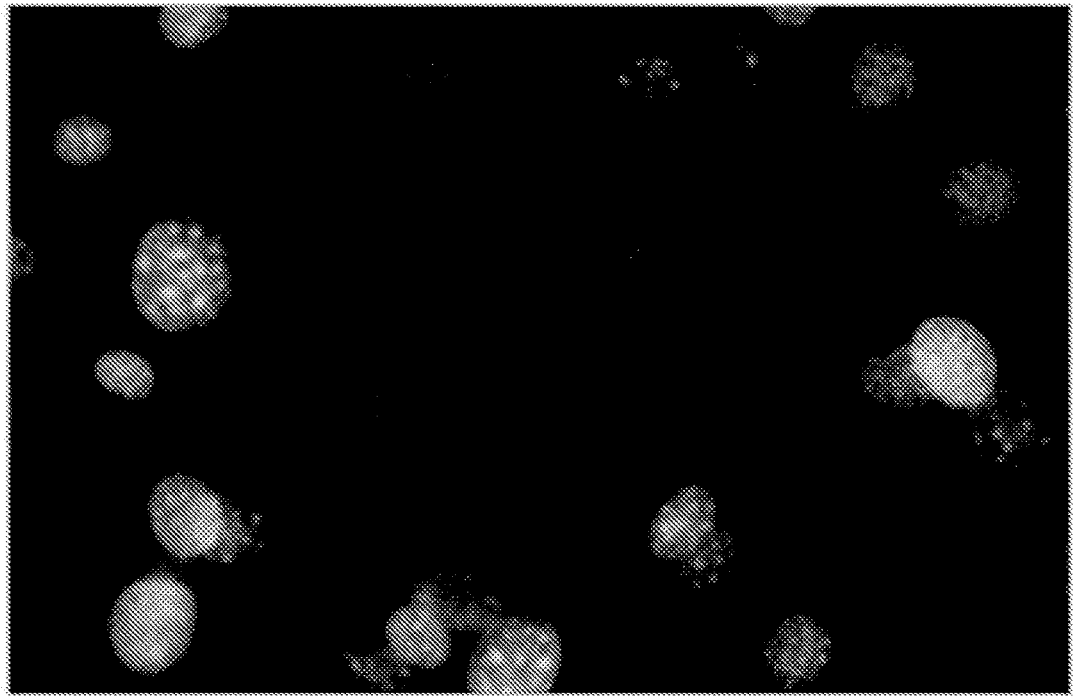
FIG. 3 is a panel of images showing distinctive nuclei morphology. Hepatocytes in co-culture with J2-3T3 fibroblasts were distinguished based on nuclei morphology. Hepatocyte nuclei (left) were smaller, rounder and more uniform in texture while fibroblast nuclei (right) were larger, more elliptical, and more punctate. Differences in species and cell type of the hepatocyte and fibroblast may account for differences in nuclei morphology.
Figure 3:
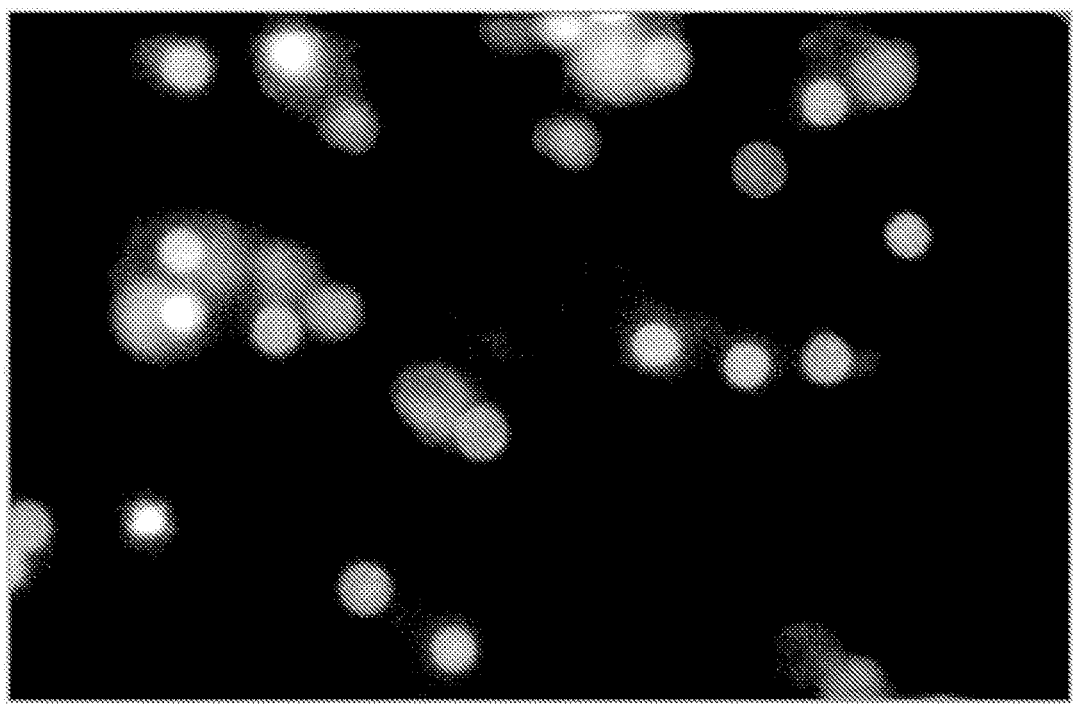
Figure 4:
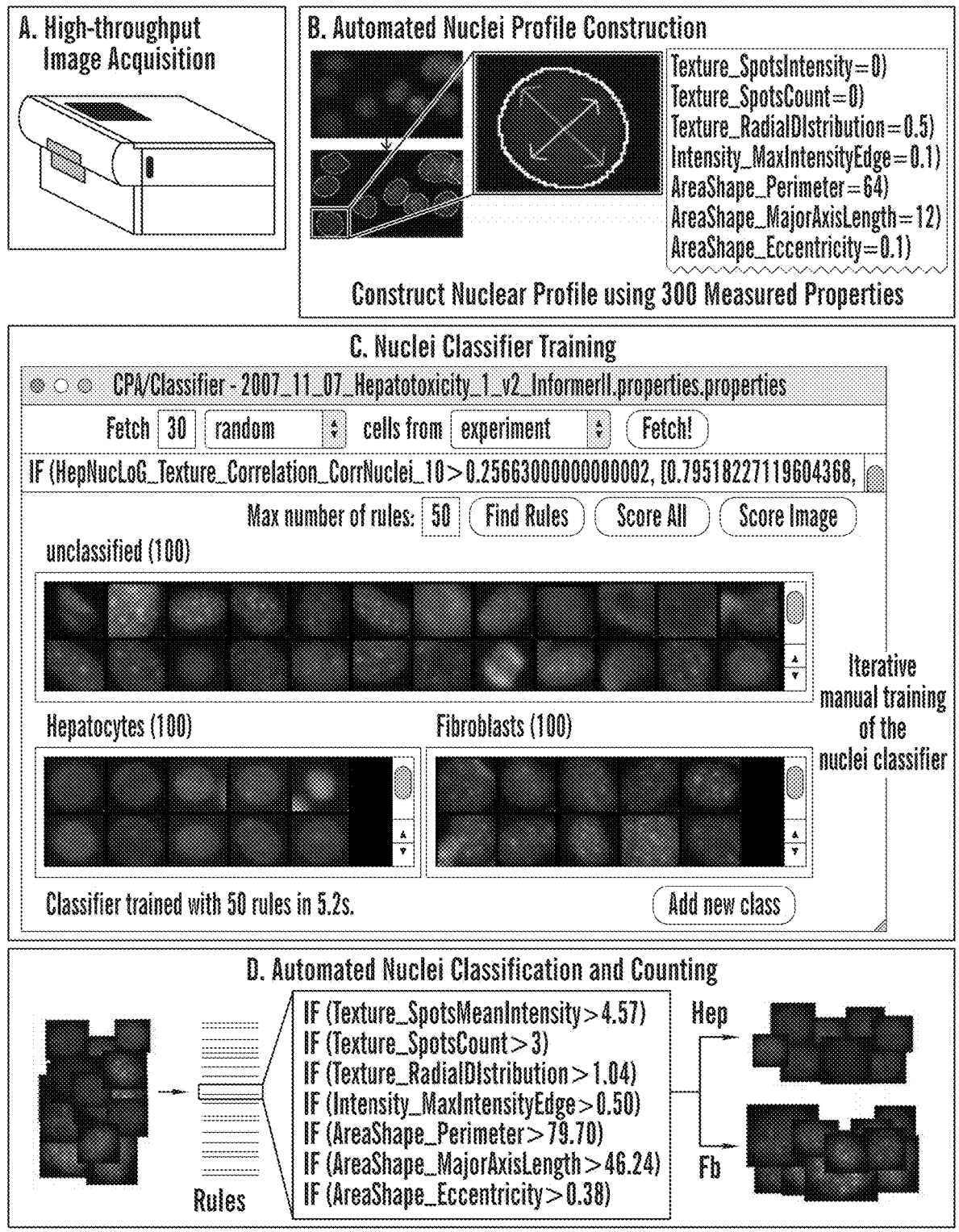
FIGS. 4A-4D shows the image-based assay workflow.

Hepatocytes in culture can be distinguished from underlying J2-3T3 fibroblasts via a variety of methods, including phase-contrast microscopy, staining for hepatocyte-specific markers, such as Albumin and CD44, and striking differences in nuclear morphology. Brightfield images, while easy to acquire, are difficult to quantify, particularly in a high-throughput manner Immunofluorescent staining of particular antigens, while easy to measure in an automated fashion, are difficult to execute in 384-well and smaller formats. Therefore, an image-based proliferation assay was developed that used nuclear morphology to quantify hepatocyte nuclei numbers in culture. When visualized with Hoechst stain, hepatocyte nuclei (FIG. 3, left image) were more uniform in texture while fibroblast nuclei are punctate (FIG. 3, right image). The assay thus visualized all cell nuclei (FIG. 4A) in culture using a simple Hoechst stain (FIG. 4B), specifically identified hepatocytes based on nuclear morphology (FIG. 4C) and provided a count of the number of hepatocyte nuclei in culture (FIG. 4D).

It should be noted that primary hepatocytes have been known to exist in multi-nucleated states and/or initiate cell cycle without completing cytokinesis. Thus this assay was not strictly a measure of hepatocyte expansion. However, cellular proliferation cannot occur without DNA synthesis. The image-based assay was designed to minimize the loss of active molecules to false negative errors during primary screening as they cannot be recovered later on; On the other hand, false positive molecules that induce DNA synthesis and/or multi-nucleation without cellular expansion can be filtered away during secondary screening, in vitro or in vivo hit validation.

Figure 5:
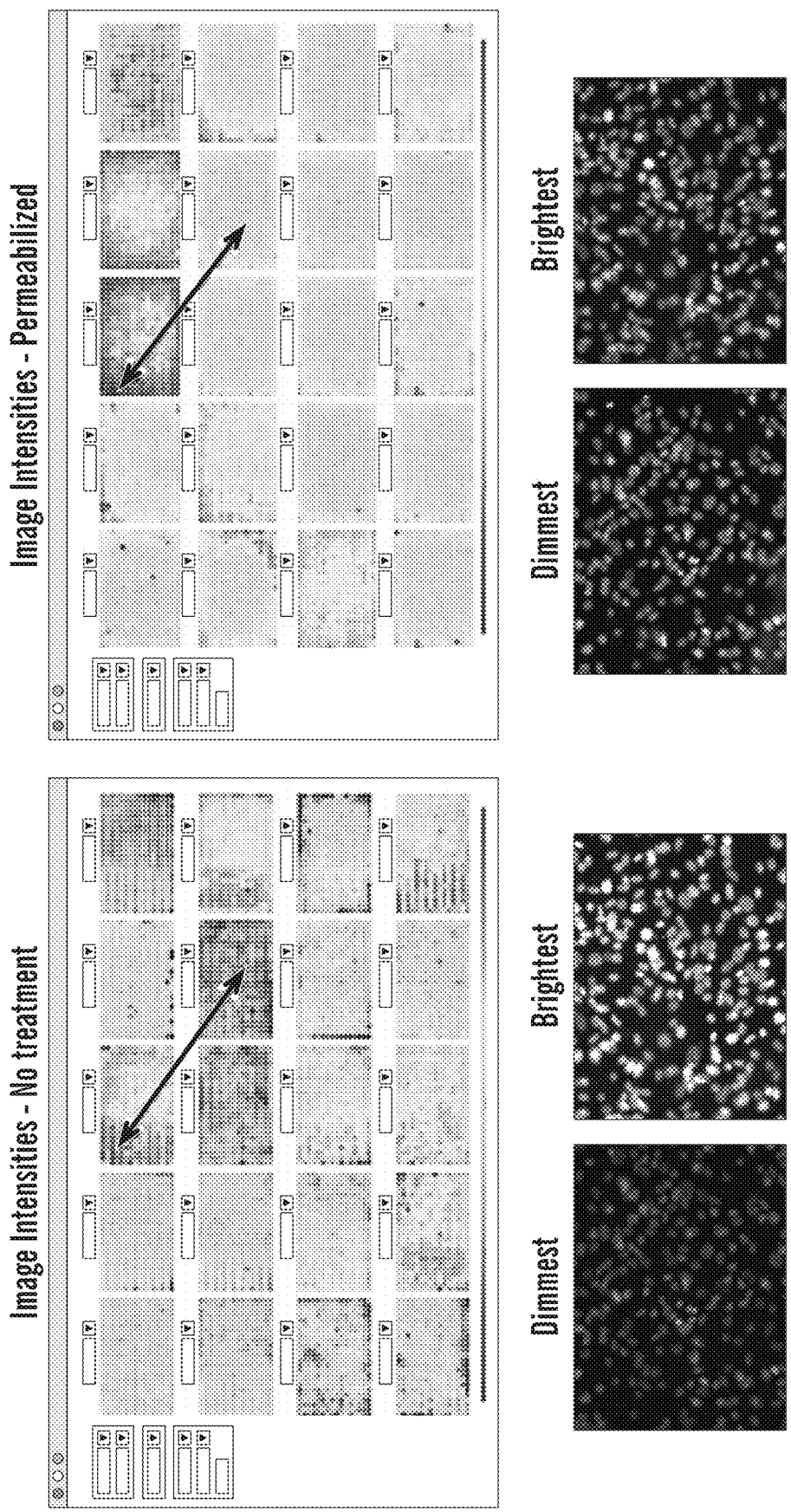
FIG. 5 is a panel of images showing uniformity of image intensity throughout the screen. Permeabilization treatment was not necessary for traditional Hoechst staining but helped normalize Hoechst 33258 staining intensities throughout screening. Upper panel shows heatmap of image intensities for each 384-well plate; arrows indicate location of brightest and dimmest images. Bottom panel shows acquired images.
Figure 6:
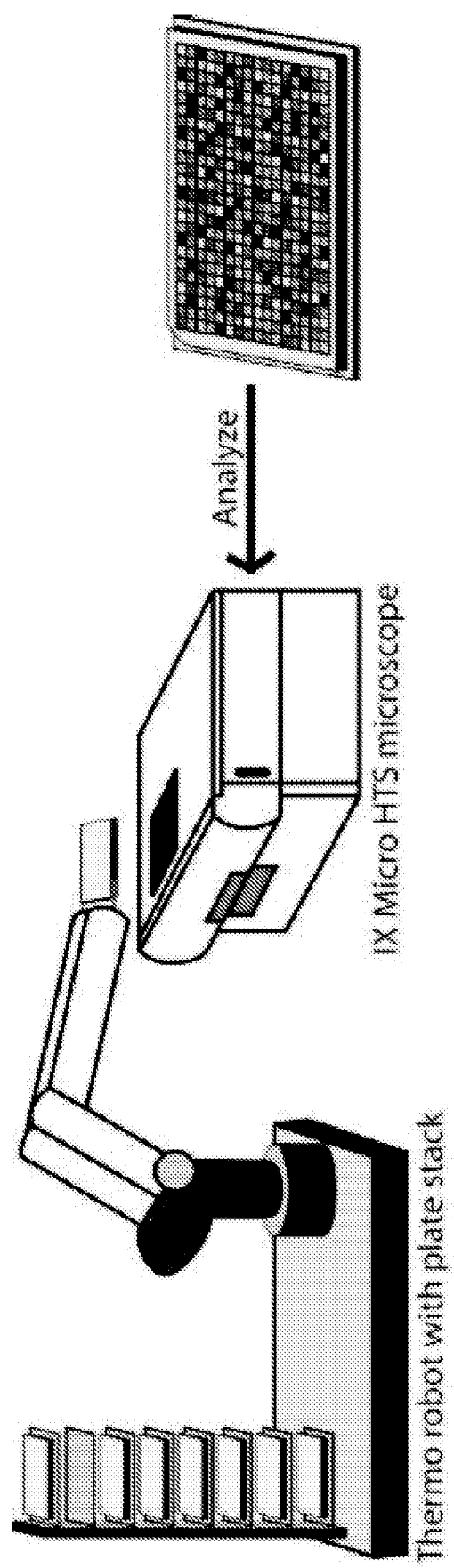
FIG. 6 is a schematic representation of the automated image acquisition. Treated sample plates were robotically loaded into a high-throughput screening microscope.

Cultures of hepatocytes and J2-3T3 fibroblasts were fixed using 4% paraformaldehyde (PFA) in black-walled, clear and flat-bottomed 384-well plates (Corning). Fixed samples were then stained with Hoechst 33342. Of note is that the cell membrane was much more permeable to Hoechst 33342 than Hoechst 33258; thus an additional permeabilization step using 0.1% Triton-X for 30 minutes was necessary when visualizing nuclei with Hoechst 33258. Without membrane permeabilization, Hoechst 33258 led to heterogenous staining intensities, which lowered the accuracy of subsequent image analyses (FIG. 5). Images of fluorescently labeled nuclei were acquired and digitized using a high-throughput screening microscope (Molecular Devices DM) coupled to a barcode reader and robotic arm (Thermo) for automated plate loading (FIG. 6). The microscope was configured to self-focus, first using lasers to identify the bottom of wells via differences in the refractive index of plastic and fluids, then using image-based focusing algorithms that scanned through a z stack of ~200 µm in ~50 µm steps in search of the plane with the sharpest images.

In earlier implementations of this image assay, the distinction of hepatocytes from fibroblasts was explored using z-position alone, but the differences between the two layers of the co-culture was too minute (~5 µm). The greater number of fibroblast nuclei (8,000 fibroblasts vs. 2,000 hepatocytes) and their punctate nature ensured automated focusing on the fibroblast plane, further enhancing the morphological differences between hepatocytes and fibroblasts to facilitate subsequent image analyses. Self-focus mechanisms did occasionally fail, burying populations of blurred images among successful acquisitions, depressing the accuracy of hepatocyte nuclei counts. To address this, subsequent analyses pipelines were developed to flag the occurrence of these normally rare failures using blurry nuclear morphologies.

Accurate examination of nuclear morphology required image acquisition at 20× magnification. Given the large volume of images required to cover 100% of well area at this high magnification, 50% of the well area in a checkerboard fashion was sampled, imaging a total of 13 sites per well. To speed up image acquisition, laser-based focusing occurred once per plate and image-based focusing executed once per well.

Automated image analysis pipelines were developed to identify every nucleus in every Hoechst-stained image of the screening cultures, and to measure various characteristics (e.g. shape, size, intensity, proximity, texture) of each nucleus using the open-source CellProfiler software.

An important first step in image processing was illumination correction. Illumination varied, in some instances, by more than 1.5-fold across a field of view, despite the use of fiber optic light sources. This added an unacceptable level of noise, and compromised the accuracy of subsequent analyses involving object intensity, including nuclei identification and classification. Thus for the proliferation assay, the CellProfiler was configured to stack all acquired images from a single experiment to identify and normalize consistent discrepancies in the staining intensities across the field of view.

Nuclei identification or segmentation was challenging when source images were crowded or, in this case, also contained overlapping objects. The accuracy of this step played a central role in determining the accuracy of the resulting nuclei counts. A variety of object identification modules offered within CellProfiler were tested, starting with a modular strategy that first identified object edges based on intensity, then separated clumped objects based on their measurements such as shape or size. This module offered a great degree of versatility, allowing customization of a number of parameters such as expected object size and intensity thresholds. While this module was configured to successfully identify crowded nuclei, an accurate segmentation of overlapping objects was difficult. Therefore, a custom module of nuclei segmentation was assembled.

Figure 7:
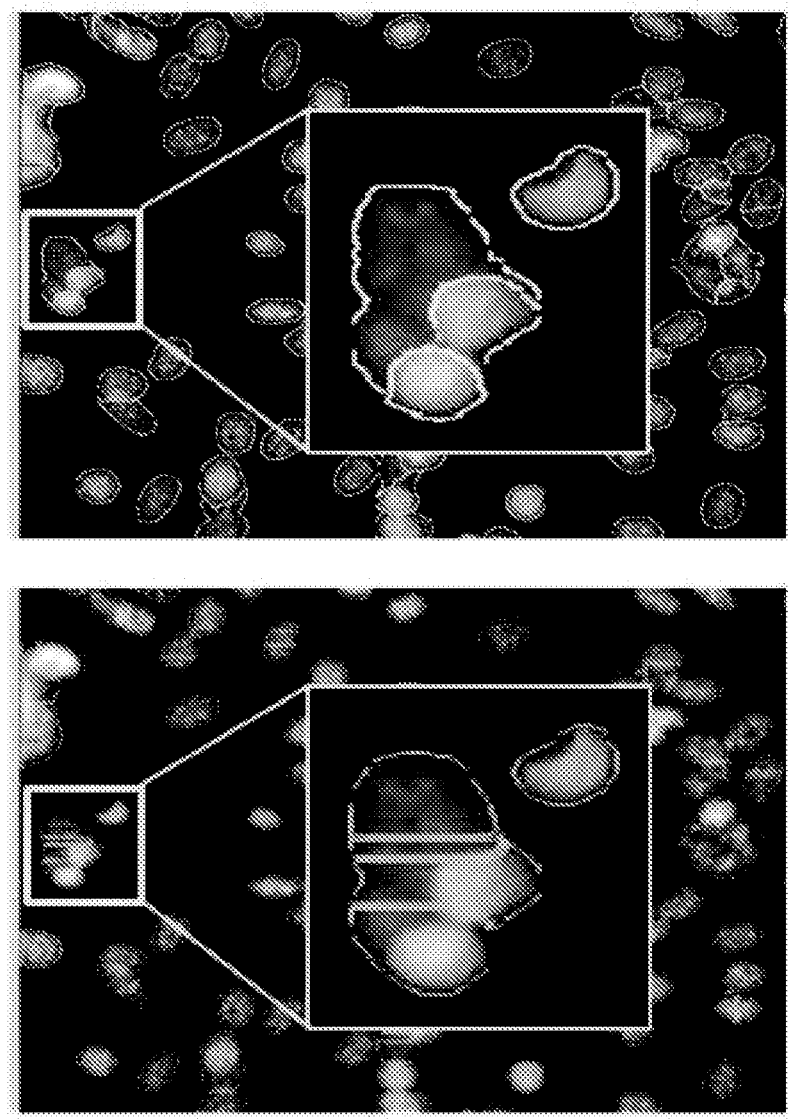
FIG. 7 shows representative images of nuclei identification. The feeder layer co-culture led to overlapping objects in Hoechst images that proved challenging to segment. The final algorithm was able to correctly identify nuclei locations and borders.

The segmentation pipeline implemented in the proliferation assay first used relative peaks in intensity to pinpoint positions of potential nuclei, so that overlapping nuclei could be correctly identified as separate objects. After the locations of nuclei were found, their edges could then be outlined more accurately using Propagation algorithms. Test modules were implemented that compared several algorithms side by side in order and incorporated into the pipeline the most accurate segmentation algorithm (FIG. 7).

Figure 8:
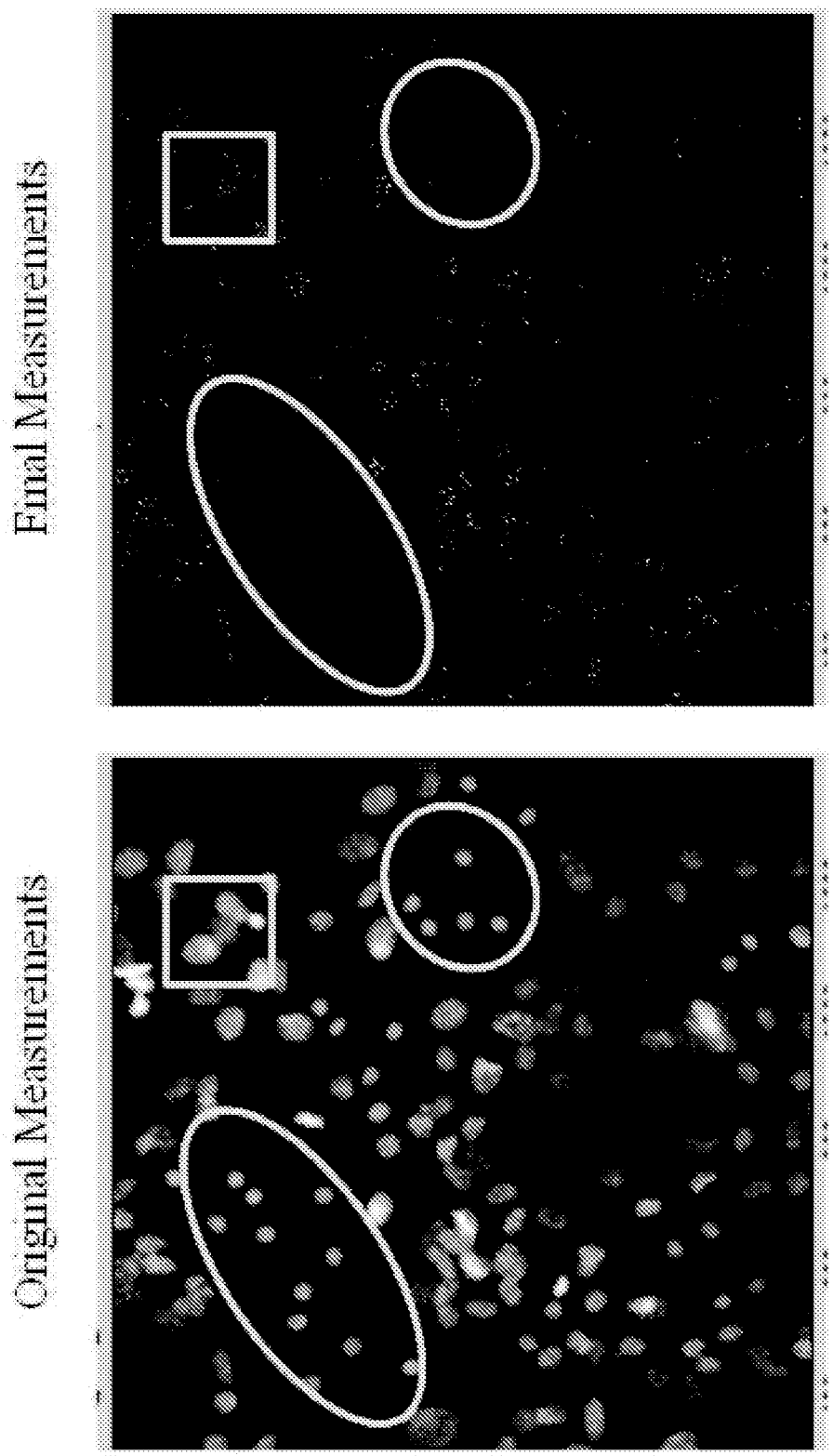
FIG. 8 shows images of sub-nuclear structure identification. Punctate sub-nuclear structures were identified as objects and associated with their parent nucleus. Circles indicate hepatocyte islands. The square surrounds one region of fibroblast cluster.

For each identified nucleus, a large number of features were measured to construct a nuclear profile, including nuclear size, shape, intensity, proximity, and texture. This profile was subsequently used to train machine learning algorithms to automatically classify nuclei as hepatocytes or fibroblasts. During assay development, nuclear morphology was observed to most effectively distinguish fibroblast nuclei from hepatocyte nuclei as there were punctate sub-nuclear structures present in fibroblasts, but absent in hepatocytes. Unfortunately, these punctate structures, while numerous, were very small, thus occupying only a minute percentage of the nuclei area; consequently, their impact on the measurements at the whole-nucleus level was too dilute for effective machine training. To address this, an additional segmentation module was included that identified the punctate sub-nuclear structures and measured how many and what type (e.g. big or small, bright or dull) of punctuates were associated with each nucleus (FIG. 8).

The nuclear profiles generated by CellProfiler were inputted into CellProfilerAnalyst178 for training of machine learning algorithms to distinguish and count hepatocyte nuclei. The training phase was manually initiated by identifying a few hepatocytes and a few fibroblasts. To avoid over-fitting the machine learning algorithm to a few particular samples, the initial training sets were populated with ~50 hepatocytes and ~50 fibroblasts taken randomly from the general population without references to specific wells or plates. Using this initial training set, a machine learning algorithm was used to generate a preliminary set of rules for nuclei classification, using the GentleBossting algorithm applied to regression stumps. This rule set was used by CellProfilerAnalyst to classify a new batch of nuclei, outputting the results for manual error correction. The corrections were then used to refine the rule set in an iterative process until an accuracy plateau is reached. Once finalized, the rule set was applied to the nuclear profiles of every nucleus of every image in the experiment to classify each object as a hepatocyte or fibroblast before outputting a count of each nucleus type per well.

Figure 9:
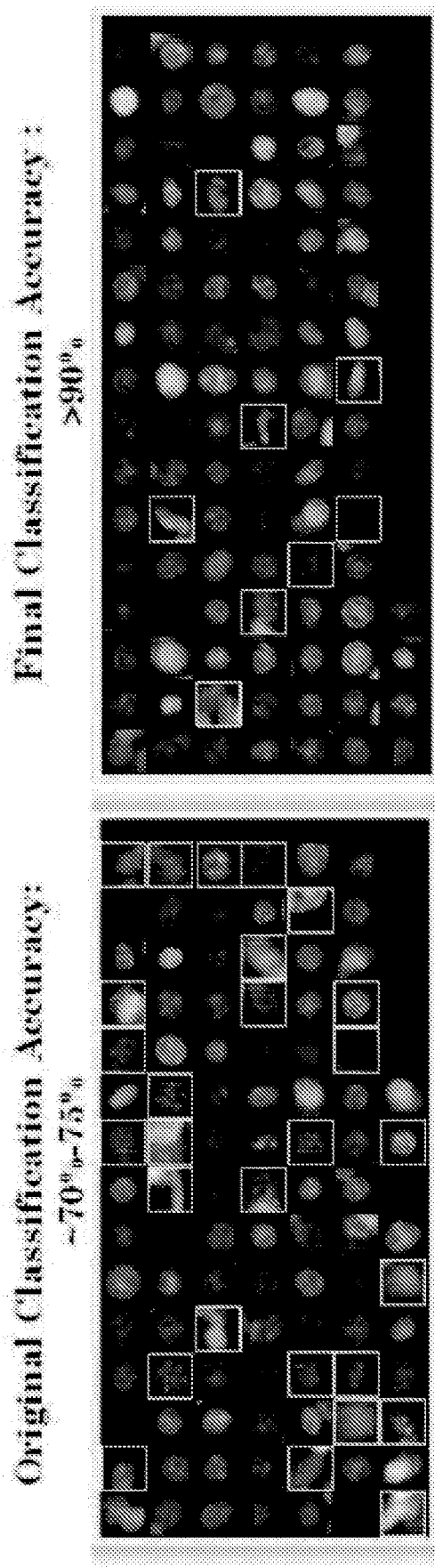
FIG. 9 is a schematic representation showing the classification accuracy. Screening images were classified without (left) and with (right) the identification of punctate sub-nuclear structures. The squares indicate fibroblast nuclei that were erroneously identified as hepatocyte nuclei.

Initial training was conducted without info on sub-nuclear structures and required approximately 1 day to complete a training set containing ~5000 manually classified objects with an accuracy plateau of ~75% using a total of 300 rules. With the assistance of punctate sub-nuclear structures, this assay used only a few hours to generate a training set of ~500 hundred objects with an accuracy plateau of at least 90%, often 95%, using a total of 100 rules (FIG. 9).

Assay readiness for high-throughput screening is most often assessed via statistical parameters such as z'-factor179, which reflects both assay signal dynamic range and variation, and is mathematically defined:

$$Z' = 1 - \frac{(3\sigma_{c+} + 3\sigma_{c-})}{|\mu_{c+} - \mu_{c-}|}$$

where "c+"=positive control, "c−"=negative control, "σ"=standard deviation and "μ"=average. Assuming normal distribution, assays with positive z'-factors can separate 99.8% of the negative and positive control populations (i.e. the two populations, as defined by mean signal+/−3 standard deviations, do not overlap), essentially separating signal from noise.

Imaging of multiple 384-well plates containing untreated hepatocyte-fibroblast co-cultures showed that the image-based readout can confidently (Z'>0) detect doublings in hepatocyte nuclei numbers with low variance (CV<20%) and good reproducibility. It should be noted, however, that the highly textured nature of fibroblast nuclei rendered their segmentation difficult, often leading to the breakup of a single nucleus into multiple nuclei. Therefore, while the assay did report numbers of fibroblast nuclei as well as hepatocyte nuclei, it was optimized for accurate detection of hepatocyte nuclei.

Figure 10:
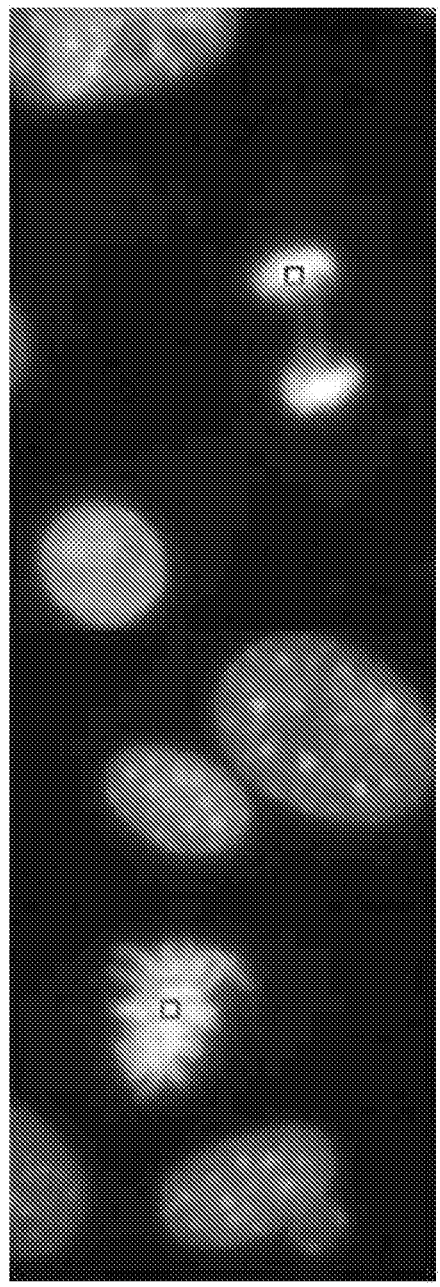
FIG. 10 is an image showing mitotic nuclei morphology. The left square marks a nucleus with morphology consistent with metaphase; the right square marks a nucleus with morphology consistent with anaphase.

In addition to quantifying hepatocyte nuclei in interphase, two additional analyses were developed to quantify the number of nuclei in the process of mitosis. These analyses were built to detect nuclear morphologies consistent with cells undergoing metaphase and anaphase (FIG. 10). While CellProfilerAnalyst was capable of simultaneously identifying more than 2 morphologies, its classification accuracy became significantly impaired with each additional category, thus separate training sets were generated for each morphology of interest (i.e. metaphase nuclei, anaphase nuclei and hepatocyte nuclei in interphase).

Cells undergoing metaphase have very distinctive nuclear morphologies and were easily quantifiable using the image assay outlined earlier in this section. Cells undergoing anaphase unfortunately assumed very similar morphologies to staining/camera artifacts, with just one distinction: anaphase nuclei always appeared in closely positioned pairs. Therefore, minor adjustments were made to the measurements of these objects to include neighbor relationships.

Training of automated nuclei classification was also altered slightly to accommodate the rare nature of these mitotic bodies. Instead of populating the training set extensively with randomly selected objects, which would result in a severely imbalanced training set containing thousands of negative examples but only a few positive items, iterative error correction was focused on.

Validation of mitotic body detection was conducted manually through visual inspection of raw images due to the lack of a positive control that can induce proliferation of primary human hepatocytes. In general, program reported counts of mitotic bodies were in agreement with manually obtained values.

In addition to the above image-based proliferation assay, the high-throughput liver platform was equipped with several functional assays in order to probe whether hepatocytes in the platform retained their liver identity. Due to the diverse repertoire of the 500+ documented and yet unidentified biochemical functions of the liver, there does not exist a single all-inclusive, gold-standard assay for measuring hepatocyte functions. Thus 3 major types of liver functions were sampled: 1) ELISA-based quantification of albumin output as a surrogate marker for protein synthesis functions of the liver, 2) colorimetric assay quantifying urea generation as a surrogate marker for amino acid metabolism functions of the liver, 3) enzyme activity assay measuring cytochrome P450 activity as a surrogate marker for detoxification functions of the liver.

Figure 11A:
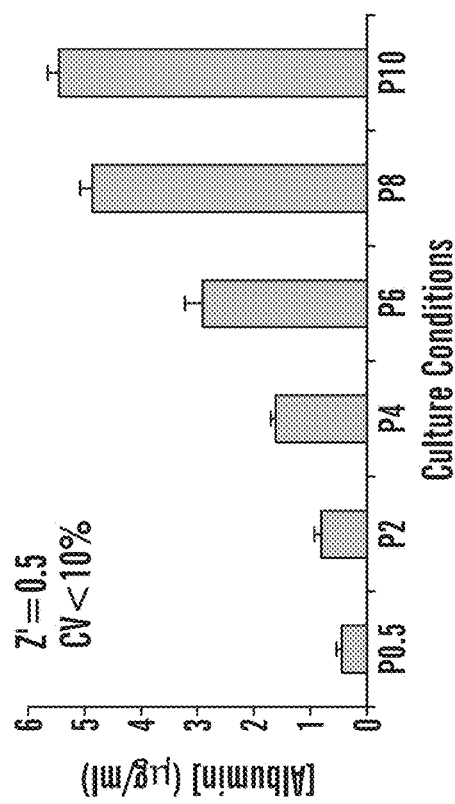
FIG. 11A is a graph showing biochemical functional assay for albumin secretion as a function of hepatocyte density in screening cultures. All data are presented as mean±standard deviation.
Figure 11C:
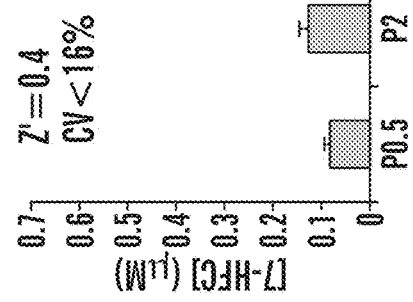
FIG. 11C is a graph showing biochemical functional assay for cytochrome P450 activity as a function of hepatocyte density in screening cultures. All data are presented as mean±standard deviation.
Figure 11B:
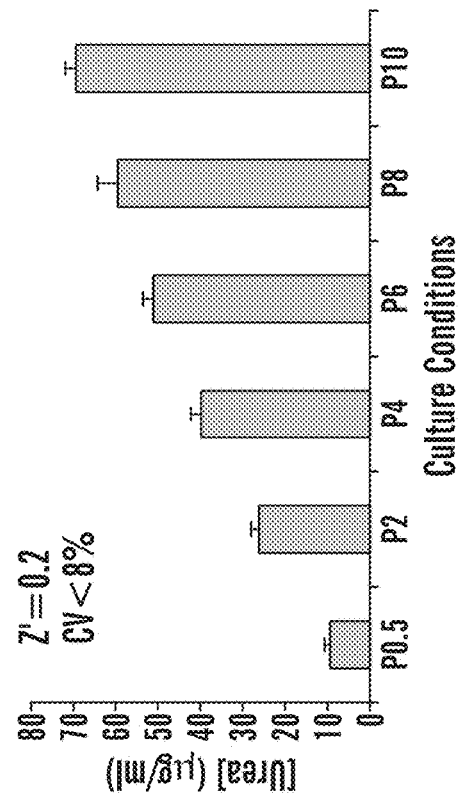
FIG. 11B is a graph showing biochemical functional assay for urea production as a function of hepatocyte density in screening cultures. All data are presented as mean±standard deviation.

For all 3 assays, parameters were optimized, such as reagent type, concentration and volume to develop them into biochemical assays compatible with high-throughput screening, with Z'>0 and wide dynamic ranges of detection (FIGS. 11A, 11B and 11C). Ultimately, for screening purposes, it is neither necessary nor practical to implement all 3 assays, thus the ELISA-based albumin quantification was chosen as the functional assay for the human liver platform.

Figure 12:
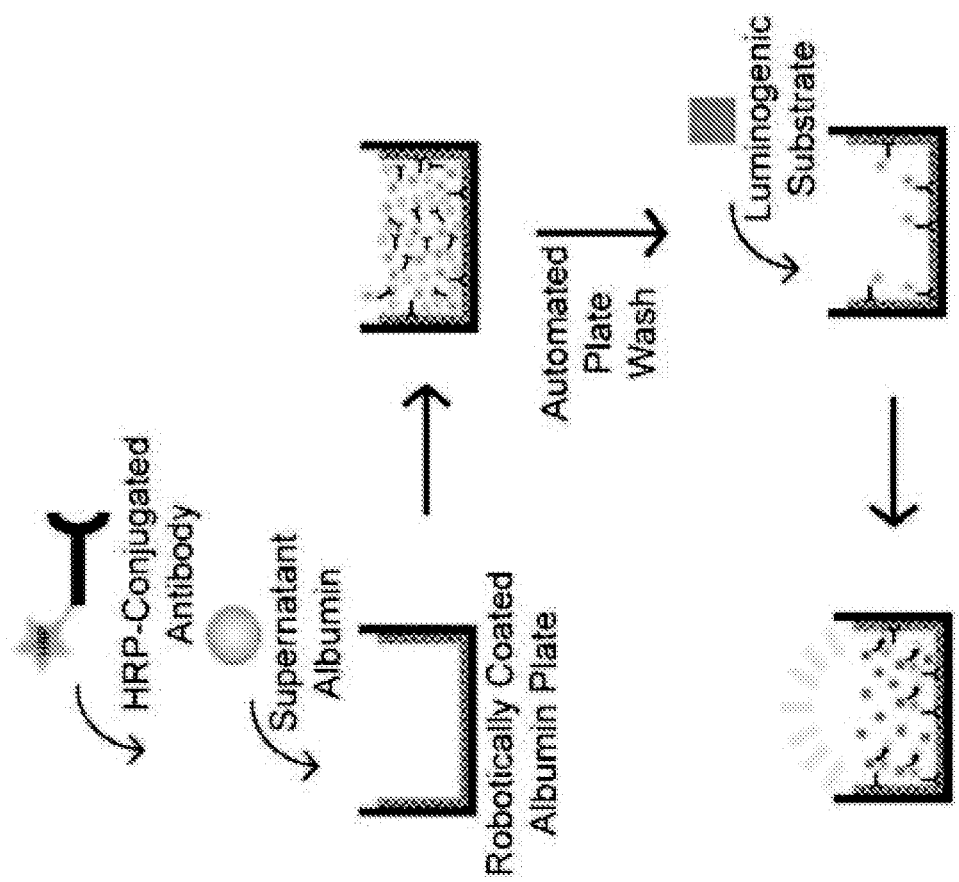
FIG. 12 is a schematic representation of a competitive ELISA.

The most common form of the ELISA assay is a sandwich ELISA that captures the antigen of interest in between 2 layers of antibodies. This assay is difficult to adapt to high-throughput screening due to the long protocol, which limits through-put, and the extensive washes, which are difficult to program robotically. Therefore, for the liver platform, a competitive ELISA assay was employed, which reduced the length of workflow by approximately a third. A saturating amount of human albumin was first coated onto the walls of adsorptive 384-well plates. Sample supernatant was then introduced and competed with coated albumin for binding to HRP-conjugated antibodies. The amount of bound antibodies was then quantified via a colorimetric substrate. Automation of the ELISA assay necessitated a few adjustments to the platform. Volume of media used to maintain cultures was increased to 30 ul/well in order to allow withdrawal of 20 ul of sample without disturbing the cell layer. An adhesive breathable membrane was added to the top of culture plates to minimize edge effects arising from fluid evaporation. The visualization agent was changed from TMB to an ultra-sensitive luminescent substrate to increase sensitivity (FIG. 12). Ultimately, validation data showed that this biochemical functional assay confidently (Z'>0) detected doublings in hepatocyte populations with low variance (CV<10%) and good reproducibility.

Predictive high-throughput liver models are a critical tool for research and development of novel therapeutics as well as for the study of liver biology. Co-cultivation of hepatocytes with J2-3T3 fibroblasts represents a scale-able platform that can maintain primary human hepatocytes in culture for at least 9 days, providing both time and space for a wide range of cellular activities. The miniature feeder layer co-culture platform described herein for primary human hepatocytes and attendant assays are useful for probing multiple hepatocyte phenotypes including cellular proliferation, cell death, protein synthesis functions, detoxification functions and amino acid metabolism.

Example 3

Design of a Primary Human Hepatocyte Co-Culture for Chemical Screening

A high-throughput liver platform was developed to enable unbiased chemical screening on primary human hepatocytes. The screen was designed to identify compounds that could induce functional proliferation and/or differentiation of the hepatocyte in order to generate renewable sources of functional human hepatocytes. The treatment of cells with small molecules has been shown to modulate a wide range of cellular processes. These processes include stem cell self-renewal and differentiation, and the proliferation of normally quiescent mature adult cells, such as pancreatic β-cells and cardiomyocytes. Compounds can act through a variety of mechanisms to induce cell division, including activation of developmental signaling pathways such as Wnt or recruitment of GEFs to the plasma membrane for RAS/MAPK pathway activation.

The accuracy and power of a high throughput screening (HTS) is determined largely by the quality of the biological platform and assay readouts. Thus, a robust screening platform was developed for primary human hepatocytes.

In order to avoid species-specific differences and cell line mutations, the screen was conducted with human primary hepatocytes. Traditionally, chemical screening on such cells has been hindered by their availability in large quantities as well as their rapid loss of viability and phenotype in vitro. Recent advances in cryopreservation technologies allowed enough primary human cells to be stored for screening, and to maintain these cells, the hepatocytes were co-cultivated with non-parenchymal cells. Co-cultures of primary human hepatocytes with murine embryonic J2-3T3 fibroblasts were recently shown to maintain normal hepatocyte phenotype for weeks. These in vitro platforms consisted of hepatocytes surrounded by a co-planar population of fibroblasts. While capable of stabilizing hepatocyte functions in vitro, such platforms may limit normal hepatocyte expansion due to contact inhibition. Thus, to provide surface area for hepatocyte expansion, a sparse population of hepatocytes was co-cultivated on top of a confluent feeder layer of J2-3T3 fibroblasts within 384-well plates. This screening platform stabilized hepatocyte phenotypic functions in vitro and was compatible with two separate high-throughput readouts developed for this screen.

Figure 13:
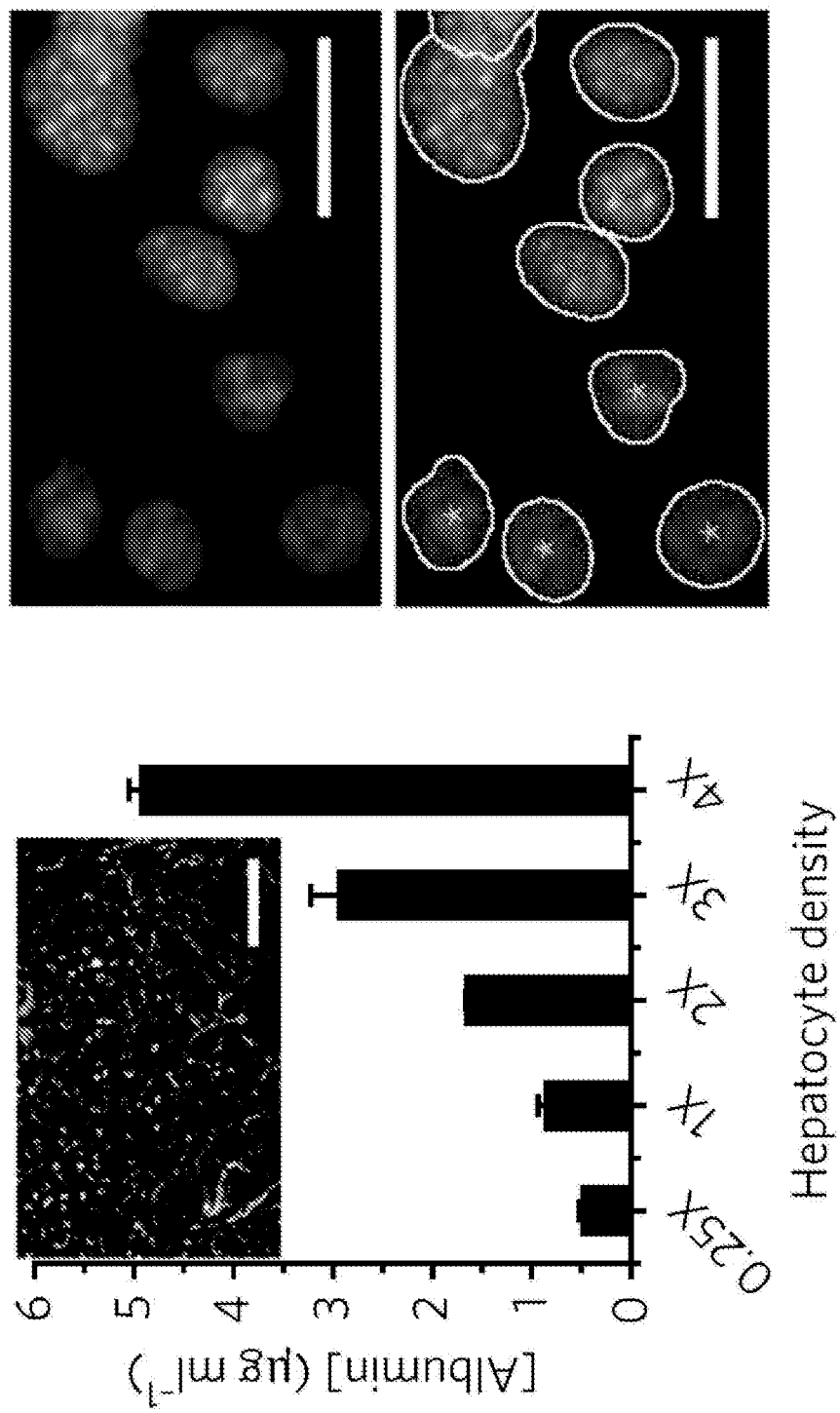
FIG. 13 is a series of graphs and high content images which show that the screening platform stabilized hepatocyte phenotypic function in vitro. The bar graph shows albumin secretion as a function of hepatocyte density in screening cultures. The inset above the bar graph is a phase-contrast image showing the morphology of the feeder-layer cocultures (scale bar, 100 μm). Hoechst staining of screening cocultures showing that hepatocyte nuclei (four left circles) have a uniform texture, whereas fibroblast nuclei (four right circles) are punctate (scale bars, 50 μm). An automated high-content imaging assay identifies and classifies individual nuclei.

The primary readout detected hepatocyte proliferation via automated high-content imaging. This assay quantified hepatocyte nuclei numbers, using nuclear morphologies to separate the hepatocyte and fibroblast sub-populations that co-exist within the screening platform. When visualized with Hoechst stain, hepatocyte nuclei were smaller and more uniform in texture, while fibroblast nuclei are larger and punctated (FIG. 13). Leveraging this distinction, automated image analyses was developed that utilized machine learning algorithms to classify nuclei types and tabulate hepatocyte nuclei numbers. Assay validation data showed that this image-based readout can confidently (z'>0) detect doublings in hepatocyte nuclei numbers with low variance (CV<20%) and good reproducibility. In addition to quantifying hepatocyte nuclei that have completed mitosis, the number of nuclei in the process of mitosis were also found and quantified. Two additional analysis pipelines were built to detect nuclear morphologies consistent with cells undergoing metaphase and anaphase.

In order to evaluate the phenotype of treated cells, a secondary readout was included to quantify hepatocyte functions via competitive ELISA. This biochemical assay measured the level of secreted albumin as a marker for protein synthesis functions of the cultured hepatocytes (FIG. 13).

Example 4

Design of Image-Based Proliferation Assay Workflow

To detect hepatocyte proliferation, a proliferation readout that can separate the hepatocyte and fibroblast sub-populations that co-exist within the co-culture was developed (FIG. 4A). The proliferation readout detected hepatocyte proliferation via a customized, automated, high-content imaging protocol. In brief, the assay quantified the number of hepatocyte nuclei, using nuclear morphologies to distinguish the hepatocyte and fibroblast sub-populations that co-exist within the screening platform. When visualized with Hoechst stain, hepatocyte nuclei were more uniform in texture while fibroblast nuclei were punctate (FIG. 4B). An automated image analysis pipeline was developed that identified every nucleus in every Hoechst-stained image of the screening cultures, and to measured various characteristics (e.g. shape, size, intensity, proximity, and texture) of each nucleus using the open-source CellProfiler software. Manual classification of randomly presented nuclei and error correction of machine-classified nuclei was incorporated into the nuclei classifier training (FIG. 4C). These characteristics morphologies were used to train machine learning algorithms to identify and count the number of hepatocyte nuclei in each image (FIG. 4D).

Example 5

Production of Co-Culture Platform and HST Screening 384-well screening plates (Corning) were incubated with a solution of type-I collagen in water (100 mg/ml, BD Biosciences) for 1 hour at 37° C. in order to allow for more secure cell attachment. A feeder layer of J2-3T3 fibroblasts were robotically plated onto the collagen at a density of 8,000 cells/well (designated as day −2), and allowed to reach confluency over 48 hours, when their growth became contact inhibited. Hydrocortisone in the culture medium curbed further fibroblast expansion to prevent overgrowth of the feeder layer.

Figure 14:
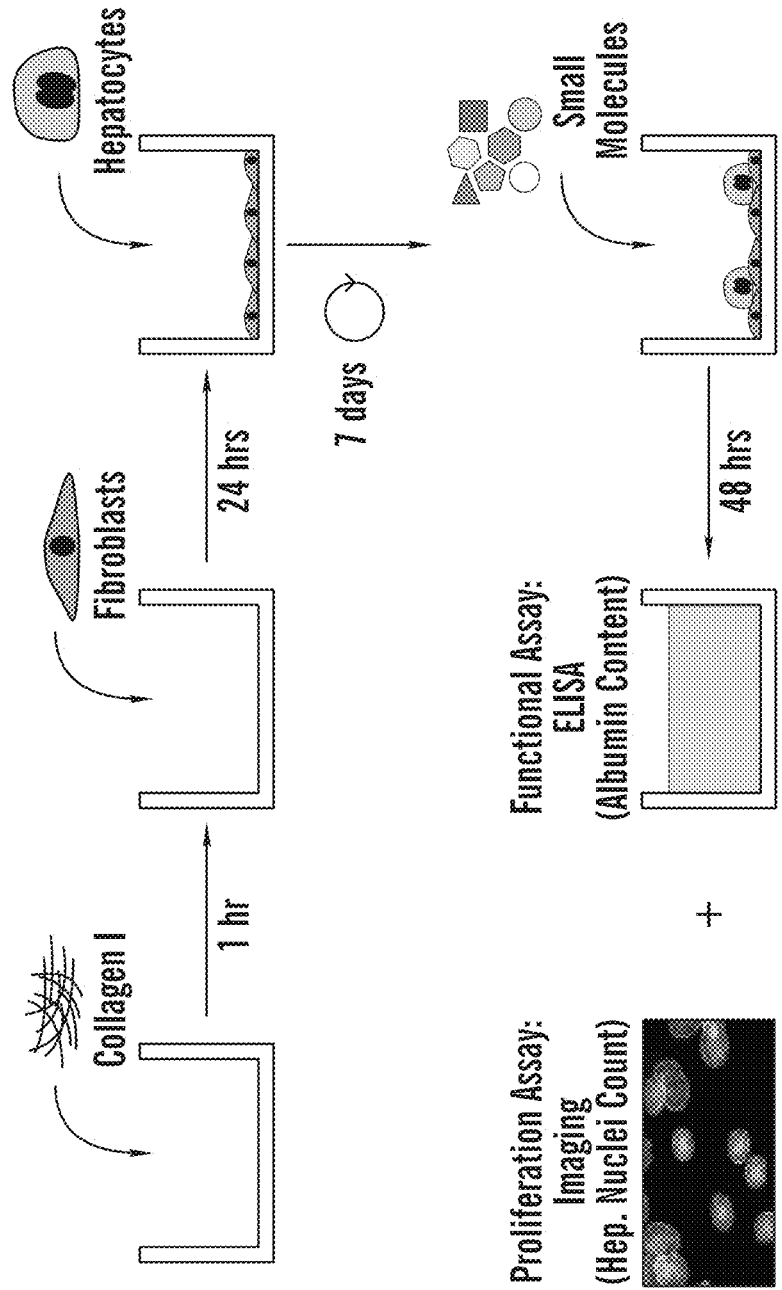
FIG. 14 is a summary of the workflow of the primary screening of small molecules.
Figure 15:
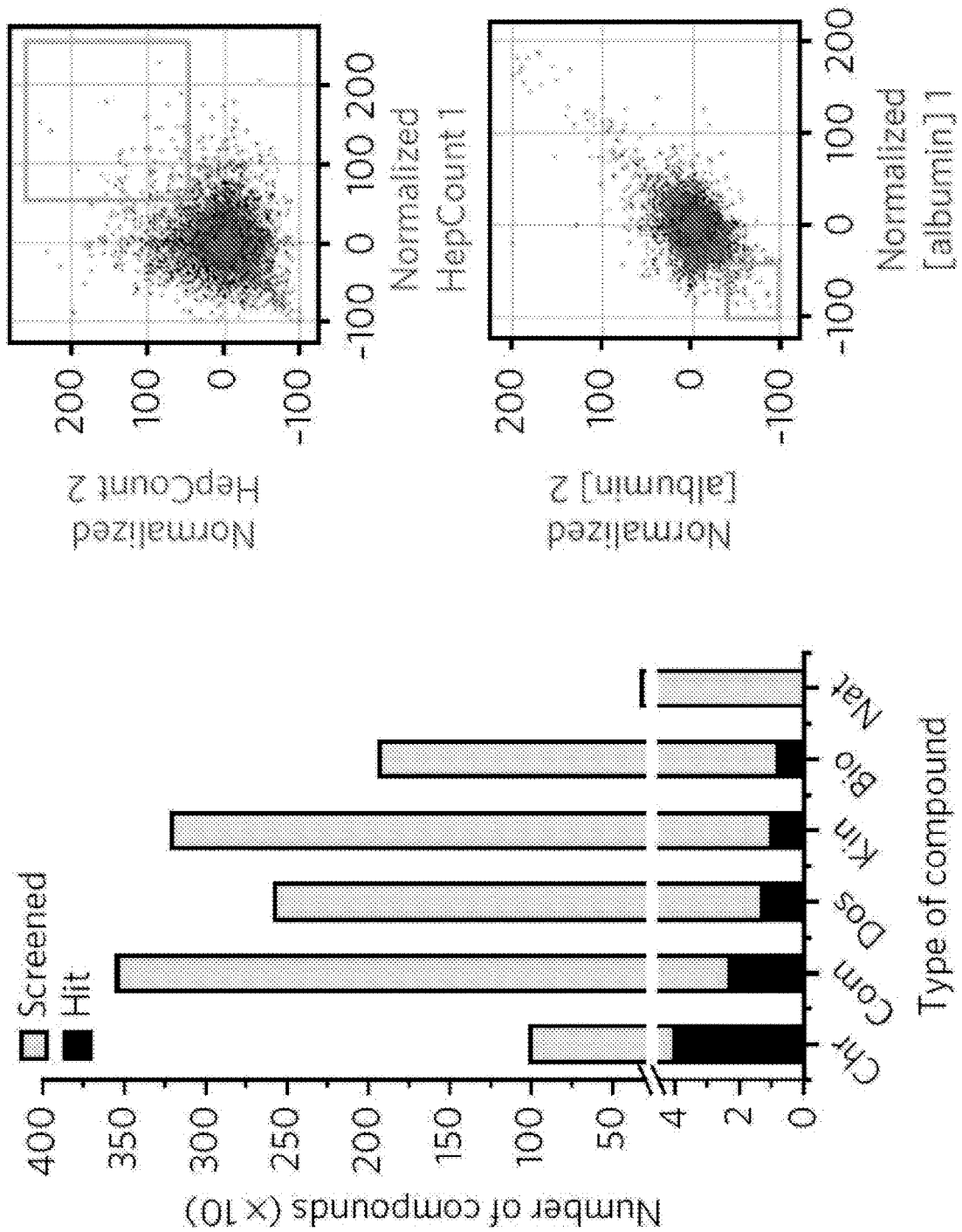
FIG. 15 is a series of graphs showing the type of compounds that constituted the initial set of 93 compounds that met all hit selection criteria qualifying as proliferation hits (FPH) and also scatterplots of primary screening data (Example 1). The bar graph shows categories of screened and hit compounds. The scatter plots display replicates of the screen, shown separately for the image-based proliferation and competitive ELISA functional readouts. Data points represent DMSO and experimental small molecules. The boxed regions indicate hit zones. Chr, chromatin-biased compounds; Com, commercially available compounds; Dos, products of diversity-oriented synthesis; Kin, kinase-biased compounds; Bio, compounds with previously documented bioactivity; Nat, natural products; HepCount, count of hepatocyte nuclei.

Primary human hepatocytes were plated onto the fibroblasts on day 0 at a density of 2,000 cells/well and maintained under standard culture conditions with daily replacement of hepatocyte medium for 7 days. Primary human hepatocytes were purchased in cryopreserved suspension from Celsis In vitro Technologies (donor a) and Invitrogen (donor b), and pelleted by centrifugation at 50 g for 10 minutes. The supernatant was discarded before re-suspension of cells in hepatocyte culture medium, which consisted of DMEM with high glucose, 10% (vol/vol) FBS, 15.6 ug/mL insulin, 16 ng/ml glucagon, 7.5 ug/ml hydrocortisone and 1% (vol/vol) penicillin/streptomycin. A library of 12,480 compounds (FIG. 14) was added on day 7 at a final concentration of ~15 uM, and allowed to incubate for 48 hours. On day 9, culture supernatants were collected for automated ELISA analysis, and cells were fixed in 4% PFA for imaging analysis (FIG. 15). Hepatocyte functions were determined via competitive ELISA (MP Biomedicals) using horseradish peroxidase detection and chemiluminescent luminol (Pierce) as a substrate. The cell-free counter assay involved ELISAs on fresh media incubated for 48 hrs with compounds of interest. Hepatocyte proliferation was assessed through customized, automated high-content imaging protocol. Fixed cells were permeabilized with 0.1% Triton-X, nuclei visualized with Hoechst stain (Invitrogen) and robotically imaged (Thermo, Molecular Devices) at 25 dispersed sites per well. Images were digitized and analyzed using CellProfiler and CellProfiler Analyst (Broad Institute).

Example 6

Methods and Materials

Luminex Analysis:
Cells were lysed using RLT buffer (Qiagen) or Trizol (Invitrogen) and purified using the Mini-RNeasy kit (Qiagen). Gene expression was determined using Luminex analysis. Briefly, total RNA was immobilized on a Qiagen turbo capture 384-well plate, and reverse-transcribed using oligo dT priming. A biotinylated FlexMap tag sequence unique to each gene of interest and a phosphorylated downstream probe were then added to resulting cDNAs to generate biotinylated FlexMap-tagged amplicons. Universal PCR was then performed for 35 cycles using a biotinylated T7 forward primer and T3 reverse primer in buffer with dNTPs and Taq polymerase. FlexMap microsphere beads conjugated with antitag oligonucleotides were then added and allowed to hybridize. Amplicons were captured by streptavidin-phyoerythrin, and 100 events per bead were analyzed for internal bead color and phyoerythrin reporter fluorescence on a Luminex FlexMap 3D analyzer. Data for replicate loadings, expressed in mean fluorescent intensity of at least 100 beads per sample, were scaled to the human transferrin gene and row-normalized for heat map representation using GeneE open software (Broad Institute).

Biochemical Assays:
Culture media were collected and frozen at −20° C. until analysis. Albumin content was measured through sandwich ELISA assays (MP Biomedicals, Fitzgerald, Bethyl Laboratories) using horseradish peroxidase detection and 3,3',5,5'-tetramethylbenzidine (TMB, Fitzgerald Industries) as a substrate. Urea concentration was determined colorimetrically using diacetylmonoxime with acid and heat (Stanbio Labs). To quantify CYP450 activity, at 48 hours after small molecule exposure, cultures were incubated with substrates (coumarin from Sigma for CYP2A6, luciferin-IPA from Promega for CYP3A4) for 4 hours at 37° C. Incubation medium was collected and metabolite concentration quantified via luminescence, or fluorescence after hydrolization of potential metabolite conjugates by β-glucuronidase/arylsulfatase (Roche, Ind.).

Cell Counting:
J2-3T3 fibroblasts were covalently labeled with Cell Tracker CM-DiI (Invitrogen) before initiation of co-culture. For FACS analysis, cells were treated with collagenase, then accutase, and suspended in PBS-0.2% FBS. Cell suspensions were supplemented with 50,000 fluorescent counting beads (CountBright, Invitrogen) per sample. Data were acquired with a 4-color flow cytometer (FACSCalibur, BD Biosciences) and analyzed with CellQuest (BD Biosciences). For Cellometer analysis, cells were trypsinized and placed on cell counting chambers (Nexcelom) for automated cell counting.

Hepatocyte Medium Composition:
1×DMEM
10% fetal bovine serum (FBS)
15.6 ug/ml insulin
7.5 μg/ml hydrocortisone
16 ng/ml glucagon
1% penicillin-streptomycin
Fibroblast Medium Composition:
1×DMEM
10% bovine serum (BS)
1% penicillin-streptomycin J2-3T3 Culture Conditions.

Passage 2 J2-3T3 fibroblasts were obtained from Howard Green (Harvard) and kept in liquid nitrogen until use. Cells were maintained under standard tissue culture conditions, in DMEM media containing 10% BS and 1% Penicillin-streptomycin. Fibroblasts were grown in T-150 tissue culture flasks and passaged 1:10 using 0.25% Trypsin-EDTA when cells reached confluency. Experiments used J2-3T3s ranging in passage numbers from P9 to P12.

Automated Cell Seeding.

Cells suspensions were diluted to the desired densities and kept in suspension using a magnetic stir bar. Thermo Combi robot was used to dispense cells into 384-well formats using speed setting low and standard cassette.

Biochemical Assays.

Urea concentration was quantified using a colorimetric assay that employs diacetylmonoxime with acid and heat (Stanbio Labs). Albumin content was measured using ELISA assays (MP Biomedicals) with horseradish peroxidase detection and TMB (Fitzgerald Industries) substrate.

Cytochrome-P450 Induction.

7-benzyloxy-4-trifluoromethylcoumarin (BFC, BDGentest) was added to cultures at 50 uM and incubated for 1 hr at 37° C. in phenol-red free media. Many different CYP450 isoforms process BFC into its fluorescent product of 7-hydroxy-4-trifluoromethylcoumarin (7-HFC), which is then quantified fluorometrically.

Automated Plate Washing.

Washing for plates containing cells were done manually to prevent cell loss. Plate washing for ELISA was performed on the BioTek ELx-405 HT, using the following optimized settings:

Prime: Prime_200 using DI water
Wash: Named program HEPELISA
Method
Number of cycles=02
Wash Format=Plate
Soak/Shake=Yes
Soak Duration=010 sec
Shake before soak=yes
Shake Duration=005 sec
Shake Intensity=4 (18 cycles/sec)
Prime after soak=No
Disp
Dispense volume=100 ul/well
Dispense flow rate=05
Dispense height=120 (15.240 mm)
Horizontal X disp pos=25 (1.143 mm)
Horizontal Y disp pos=20 (0.914 mm)
Bottom wash 1st=no
Prime before start=no
Aspir
Aspir. Height=020 (2.540 mm)
Horiz. X Asp. Pos=00
Horiz Y asp pos=00
Asp rate=05 (6.4 mm/sec)
Asp delay=0000 msec
Cross-wise aspir=yes
Cross-wise on=all
Cross-wise height=020 (2.540 mm)
Cross-wise X horiz. Pos=00
Cross-wise Y horiz. Pos=00
Final asp=Yes
Final asp. Delay=0000 msec
Automated Plate Reading.

Perkin Elmer Envision 2102 Multilabel Reader was used to quantify ELISA signal. Program named ShanMeghan Chemillum and contains integration duration of 0.1 sec, luminescence mirror, luminescence 700 emission filter and measurement height of 6.5 mm.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A co-culture for high throughput analysis of primary hepatocytes, comprising:
a layer of feeder cells disposed without aggregation in a well of a multi-well plate comprising at least 96 wells;
a layer of primary hepatocytes overlaid on the feeder cells wherein the hepatocytes are not contact inhibited and are at a density that allows for expansion of the hepatocytes in the co-culture for at least 7 days prior to a high throughput analysis; wherein the bottom surface of the well in the multi-well plate is coated with a cell adhesion substrate selected from the group consisting of collagen, fibronectin, vitronectin, laminin, entactin, Arg-Gly-Asp (RGD) peptide, Tyr-Ile-Gly-Ser-Arg (YIGSR) peptide, glycosaminoglycans (GAGS), hyaluronic acid (HA), integrins, intercellular adhesion molecules (ICAMs), selectins, cadherin, cell-surface protein-specific antibodies, and a combination thereof; and wherein the feeder cells are disposed in a single confluent layer on the cell adhesion substrate; and
culture medium in the well of the multi-well plate in an amount sufficient to support hepatocyte expansion and maintain at least one biological activity of the hepatocytes for assessment in the high throughput analysis.

2. The co-culture of claim 1, wherein the multi-well plate comprises at least 384 wells.

3. The co-culture of claim 1, wherein the hepatocytes and feeder cells are plated at a ratio of 1:4.

4. The co-culture of claim 1, wherein the hepatocyte biological activity is selected from the group consisting of albumin secretion, liver-specific protein synthesis, bile production, detoxification of compounds, energy metabolism, and cholesterol metabolism.

5. The co-culture of claim 1, wherein the feeder cells and hepatocytes are of different species.

6. The co-culture of claim 1, wherein the feeder cells comprise one or more types of non-parenchymal cells.

7. The co-culture of claim 6, wherein the non-parenchymal cells are selected from the group consisting of fibroblast or fibroblast-derived cells and hepatic non-parenchymal cells.

8. The co-culture of claim 7, wherein the hepatic non-parenchymal cells are selected from the group consisting of Kupffer cells, Ito cells, endothelial cells, stellate cells, cholangiocytes and hepatic natural killer cells.

9. The co-culture of claim 1, wherein the feeder cells express a protein selected from the group consisting of Delta-like homolog 1; C-fos-induced growth factor; Ceruloplasmin; Decorin; Interferon regulatory factor 1; 204 interferon-activatable protein; Splicing factor, arginine/serine-rich 3; JKTBP; Autoantigen La; High mobility group box 1; Esk kinase; dihydrofolate reductase gene: 3' end; Pm1 protein and Rac GTPase-activating protein 1.

10. The co-culture of claim 1, wherein the culture medium comprises hydrocortisone.

11. The co-culture of claim 1, wherein the primary hepatocytes are overlaid on the feeder cells in an amount of about $5 \times 10^3$ cells/well or fewer in a multi-well plate having 384 wells.

12. The co-culture of claim 1, wherein the hepatocytes are stable in the co-culture for at least 9 days without hepatocyte crowding.

13. A co-culture platform for high throughput analysis of primary hepatocytes, comprising:
a layer of feeder cells disposed without aggregation in a well of a multi-well plate comprising at least 96 wells;
a layer of primary hepatocytes overlaid on the feeder cells wherein the hepatocytes are not contact inhibited and are at a density that allows for expansion of the hepatocytes in the co-culture for at least 7 days prior to a high throughput analysis; wherein the bottom surface of the well in the multi-well plate is coated with a cell adhesion substrate selected from the group consisting of collagen, fibronectin, vitronectin, laminin, entactin, Arg-Gly-Asp (RGD) peptide, Tyr-Ile-Gly-Ser-Arg (YIGSR) peptide, glycosaminoglycans (GAGS), hyaluronic acid (HA), integrins, intercellular adhesion molecules (ICAMs), selectins, cadherin, cell-surface protein-specific antibodies, and a combination thereof; wherein the feeder cells express a protein selected from the group consisting of Delta-like homolog 1, C-fos-induced growth factor, Ceruloplasmin, Decorin, Interferon regulatory factor 1, 204 interferon-activatable protein, Splicing factor, arginine/serine-rich 3, JKTBP, Autoantigen La, High mobility group box 1, Esk kinase, dihydrofolate reductase gene: 3' end, Pm1 protein and Rac GTPase-activating protein 1; and wherein the feeder cells are disposed in a single confluent layer on the cell adhesion substrate; and
culture medium in the well of the multi-well plate in an amount sufficient to support hepatocyte expansion and maintain at least one biological activity of the hepatocytes for assessment in the high throughput analysis.

14. The co-culture of claim 13, wherein the hepatocyte biological activity is selected from the group consisting of albumin secretion, liver-specific protein synthesis, bile production, detoxification of compounds, energy metabolism, and cholesterol metabolism.

15. The co-culture of claim 13, wherein the feeder cells and hepatocytes are of different species.

16. The co-culture of claim 13, wherein the feeder cells comprise one or more types of non-parenchymal cells.

17. The co-culture of claim 16, wherein the non-parenchymal cells are selected from the group consisting of fibroblast or fibroblast-derived cells and hepatic non-parenchymal cells.

18. The co-culture of claim 17, wherein the hepatic non-parenchymal cells are selected from the group consisting of Kupffer cells, Ito cells, endothelial cells, stellate cells, cholangiocytes and hepatic natural killer cells.

19. The co-culture of claim 13, wherein the primary hepatocytes are overlaid on the feeder cells in an amount of about $5 \times 10^3$ cells/well or fewer in a multi-well plate having 384 wells.

20. The co-culture of claim 13, wherein the hepatocytes are overlaid onto the feeder cells at a ratio of 1:4 or less.

21. The co-culture of claim 13, wherein the multi-well plate comprises at least 384 wells.

22. The co-culture of claim 13, wherein the hepatocytes are stable in the co-culture for at least 9 days without hepatocyte crowding.

* * * * *